US011104726B2

(12) United States Patent
Malanson et al.

(10) Patent No.: US 11,104,726 B2
(45) Date of Patent: *Aug. 31, 2021

(54) METHODS OF REPLICATING A LARGE SCALE ECULIZUMAB PRODUCTION CELL CULTURE

(71) Applicant: Alexion Pharmaceuticals, Inc., Boston, MA (US)

(72) Inventors: Hunter F. Malanson, Wallingford, CT (US); Pratik Jaluria, Madison, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/708,556

(22) Filed: Dec. 10, 2019

(65) Prior Publication Data

US 2020/0172606 A1 Jun. 4, 2020

Related U.S. Application Data

(63) Continuation of application No. 14/881,824, filed on Oct. 13, 2015, now Pat. No. 10,544,209.

(60) Provisional application No. 62/064,457, filed on Oct. 15, 2014.

(51) Int. Cl.
```
C12N 5/00       (2006.01)
C07K 16/18      (2006.01)
C12P 21/00      (2006.01)
```
(52) U.S. Cl.
CPC ............ C07K 16/18 (2013.01); C12N 5/0018 (2013.01); C12P 21/00 (2013.01); C07K 2317/24 (2013.01); C07K 2317/76 (2013.01); C12N 2510/02 (2013.01)

(58) Field of Classification Search
None
See application file for complete search history.

(56) References Cited

U.S. PATENT DOCUMENTS

| | | | |
|---|---|---|---|
| 6,355,245 B1 | 3/2002 | Evans et al. | |
| 10,544,209 B2 | 1/2020 | Malanson et al. | |
| 2009/0215165 A1 | 8/2009 | Rance et al. | |
| 2012/0164066 A1 | 6/2012 | Greene et al. | |
| 2013/0064820 A1 | 3/2013 | Magro | |
| 2016/0108112 A1 | 4/2016 | Malanson et al. | |
| 2016/0108357 A1 | 4/2016 | Malanson et al. | |

FOREIGN PATENT DOCUMENTS

| | | |
|---|---|---|
| WO | 2004/058944 A2 | 7/2004 |
| WO | 05/110481 A2 | 11/2005 |
| WO | 2007/062218 A1 | 5/2007 |
| WO | 2007/106585 A1 | 9/2007 |
| WO | 2010/040480 A1 | 4/2010 |
| WO | 2011137362 A1 | 11/2011 |
| WO | 2016061066 A1 | 4/2016 |

OTHER PUBLICATIONS

Albumax I, Lipid-Rich Bovine Serum Albumin, Cat. No. 11020, GIBCO Invitrogen Corporation, (2001) 1 page, [Date of retrieval: Apr. 17, 2018], http://tools.thermofisher.com/content/sfs/manuals/3118.pdf.
Alden et al. Abstract of Papers, 243rd ACS National Meeting Exposition, Mar. 25-29, 2012, BIOT-307.
Alden, N. et al. "Development of a Scale-Down Model Using the Micro24 Micro-Bioreactor System," Abstract of Papers, 243rd ACS National Meeting Exposition, Mar. 25-29, 2012, BIOT-307, Poster Presentation, 1 page.
An, Z. et al., "IgG2m4, an engineered antibody isotype with reduced Fc function," mAbs, vol. 1(6): 572-579 Nov./Dec. 2009.
Bareither, R. et al., "A Review of Advanced Small-Scale Parallel Bioreactor Technology for Accelerated Process Development: Current State and Future Need," Biotechnol. Prog., vol. 27, No. 1, pp. 2-14 (2011).
Beck, A., et al., "Trends in Glycosylation, Glycoanalysis and Glycoengineering of Therapeutic Antibodies and Fc-Fusion Proteins," Current Pharmaceutical Biotechnology, vol. 9: 482-501 (2008).
Bovine Albumin, ICP bio Ltd, (2007) 2 pages [Date of retrieval: Apr. 17 2018] (http://www.ibric.org/myboard/view.php?Board=new_protech&filename=Albumin.pdf&id=1759&fidx=1).
Bovine ICPbio International Ltd., "Product sheet of Bovine albumin," Jan. 1, 2013, 1 page (http://www.qcbio.com/icp/sharedfiles/icpbio/Documents/5565-ICP-Bovine-Albumin.pdf).
Database WPI, Week 201241, abstract, 2 pages (2012).
Fan, L. et al., "The use of glutamine synthetase as a selection marker: recent advances in Chinese hamster ovary cell ine generation processes," Pharmaceutical Bioprocessing, vol. 1(5):487-502 (2013).
Gebauer, M. et al., "Engineered protein scaffolds as next-generation antibody therapeutics," Current Opinion in Chemical Biology, vol. 13, pp. 245-255 (2009).
Hermes, P. A. et al., "A Fully Defined, Fed-Batch, Recombinant NSO Culture Process for Monoclonal Antibody Production," Biotechnol. Prog., vol. 26, No. 5, pp. 1411-1416 (2010).
ICP Biologicals: "Bovine albumin of NZ animals," Aug. 30, 2007, pp. 1-2. (URL:http://www.ibric.org/myboard/view.php?Board=new_protech&filename=Albumin.pdf&id=1759&fidx=1).
International Preliminarty Report on Patentability, PCT/US2015/055277, dated Apr. 18, 2017, 7 pages.
International Search Report and Written Opinion, PCT/US2015/055277, dated Feb. 15, 2016, 12 pages.
Jaluria, P. et al., "Iterating to a solution: Refinement of a small-scale bioreactor model," American Chemical Society, Abstracts of Papers (at the national meeting), vol. 243, 1 page (2012).
Jaluria, P. et al.,"Iterating to a Solution: Refinement of a Small-Scale Bioreactor Model," American Chemical Society, Abstract of Papers at the National Meeting, vol. 243, 2012; Mar. 25-29, 2012; BIOT-377 (1449; #3), Poster Presentation, 22 pages.

(Continued)

*Primary Examiner* — Phillip Gambel
(74) *Attorney, Agent, or Firm* — Nelson Mullins Riley & Scarborough LLP; Jane E. Remillard, Esq.; Jill Gorny Sloper, Esq.

(57) ABSTRACT

Provided herein are methods of replicating a large scale eculizumab production cell culture in a small scale culture.

20 Claims, 6 Drawing Sheets

Specification includes a Sequence Listing.

(56) References Cited

OTHER PUBLICATIONS

MP Biomedicals, "Chromatopur Product Range Training Guide," Feb. 24, 2012, 36 pages (http://58.68.249.183/files/prod/references/201208/06/11884001.pdf).

Nienow, A. W. et al., "Scale-down studies for assessing the impact of different stress parameters on growth and product quality during animal cell culture," Chemical Engineering Research and Design, vol. 91, No. 11, pp. 2265-2274 (2013).

Nienow, A. W. et al., "The physical characterisation of a microscale parallel with industrial CHO cell line expressing an IgG4," Biochemical Engineering Journal, vol. 76, pp. 25-36 (2013).

Nienow, A. W., "Re Development of a scale-down model of hydrodynamic stress to study the pertormance of an ndustrial CHO cell line under simulated production scale bioreactor conditions," Journal of Biotechnology, vol. 171, pp. 82-84 (2013).

Sieck, J. B. et al., "Development of a Scale-Down Model of hydrodynamic stress to study the pertormance of an ndustrial CHO cell line under simulated production scale bioreactor conditions," Journal of Biotechnology, vol. 164, No. 1, pp. 41-49 (2012).

Wu, Y. et al., "Enhanced productivity of NSO cells in fed-batch culture with cholesterol nanoparticle supplementation," Biotechnology Progress, vol. 27 (3), pp. 796-802 (2011).

Zhou, W., "Fed-batch culture of recombinant NS0 myeloma cells with high monoclonal antibody production," Biotechnology and Bioengineering, vol. 55: 783-792 (1997).

METHODS OF REPLICATING A LARGE SCALE ECULIZUMAB PRODUCTION CELL CULTURE

RELATED APPLICATIONS

This application is a continuation of U.S. patent application Ser. No. 14/881,824, filed on Oct. 13, 2015 (Allowed), which claims priority to and the benefit of U.S. provisional patent application No. 62/064,457, filed on Oct. 15, 2014, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 6, 2019, is named AXJ-197CN_Sequence_Listing.txt and is 6,299 bytes in size.

TECHNICAL FIELD

This invention relates to methods cell culture and the manufacture of recombinant proteins.

BACKGROUND

Eculizumab is a humanized monoclonal antibody that specifically binds to human complement component 5 (C5). Eculizumab has been approved by the FDA for treating paroxysmal nocturnal hemoglobinuria and atypical hemolytic uremic syndrome. Eculizumab is typically produced using a large scale (10,000-L) fed batch mammalian cell culture.

Small-scale models of production cell cultures provide a means for testing culture media or media components and/or mammalian cell lines prior to their use in a large scale production cell culture. Small-scale models of productions cell cultures also provide a means for testing culture media or media components and/or mammalian cell lines for contamination prior to their use in large scale production cultures. There is a need for a small scale model of the eculizumab production process.

SUMMARY

The present invention is based, at least in part, on the discovery of a set of culture parameters that allows for the accurate replication of a large scale eculizumab production cell culture using a small scale fed batch cell culture. Thus, the present specification includes methods of replicating a large scale eculizumab production cell culture using a small scale fed batch cell culture.

Provided herein are methods of replicating a large-scale eculizumab production cell culture in a small scale culture that include: providing a 4-L to 10-L bioreactor (such as a fed batch bioreactor) containing a first culture medium that occupies between about 70% and about 90% of the capacity of the bioreactor and has an initial cell density of between about $2.5 \times 10^5$ and about $7.5 \times 10^5$ NS0 cells/mL, the cells containing a recombinant eculizumab-encoding nucleic acid; culturing (such as fed batch culturing) the cells in the bioreactor for at least 8 days at about 34° C. to about 39° C., at a $dO_2$ level of between about 14% to about 16%, and a rotary agitation of between about 50 RPM and about 70 RPM; maintaining (e.g., continuing) fed batch culturing until a cell density of about $13 \times 10^5$ to about $20 \times 10^5$ cells/mL is reached, then; (1) continuously adding a feed culture medium to the first culture medium for a period of about 120 hours to about 150 hours, and about 40 to 60 hours after the start of continuous addition of the feed culture medium, and (2) continuously adding an alkali base solution to the first culture medium for a period of between about 90 hours to about 105 hours.

In some embodiments of any of the methods described herein, one or both of the first culture medium and the feed culture medium includes a processed bovine serum albumin (BSA). In some embodiments of any of the methods described herein, the processed BSA is processed New Zealand BSA. In some embodiments of any of the methods described herein, the initial cell density is between about $4.0 \times 10^5$ cells/mL and about $6.0 \times 10^6$ cells/mL. In some embodiments of any of the methods described herein, the bioreactor has a capacity of between about 4-L to about 6-L.

In some embodiments of any of the methods described herein, the first culture medium occupies between about 80% to about 88% of the capacity of the bioreactor. In some embodiments of any of the methods described herein, the fed batch culturing is performed at a temperature of about 36° C. to about 37° C. In some embodiments of any of the methods described herein, the rotary agitation is between about 55 RPM and about 65 RPM. In some embodiments of any of the methods described herein, the target cell density is between about $17 \times 10^5$ cells/mL and about $19 \times 10^5$ cells/mL.

In some embodiments of any of the methods described herein, the alkali base solution is continuously added to the first culture medium for a period of between about 92 hours to about 100 hours. In some embodiments of any of the methods described herein, the bioreactor contains 4.2 L of the first culture medium, and the alkali base solution is continuously added to the first culture medium at a rate of between about 1.65 mL/hour to about 1.85 mL/hour. In some embodiments of any of the methods described herein, the alkali base solution includes between about 0.65 M and about 0.85 M sodium carbonate and between about 0.4 M and about 0.6 M sodium bicarbonate.

In some embodiments of any of the methods described herein, a single feed culture medium is continuously added to the first culture medium. In some embodiments of any of the methods described herein, two different feed culture media are continuously added to the first culture medium. In some embodiments of any of the methods described herein, each of the two different feed culture media are continuously added to the first culture medium at a rate of between about 15 µL/minute to about 35 µL/minute. In some embodiments of any of the methods described herein, each of the two different feed culture media are continuously added to the first culture medium at a rate of between about 20 µL/minute to about 25 µL/minute. In some embodiments of any of the methods described herein, the feed culture medium is continuously added to the first culture medium for a period of between about 130 hours to about 135 hours.

Some embodiments of any of the methods described herein further include adding a bolus of a lipid solution including linoleic acid, oleic acid, and cholesterol to the first culture medium at a time point when the cells reach a density of about $13 \times 10^5$ cells/mL to about $20 \times 10^5$ cells/mL. In some embodiments of any of the methods described herein, the lipid solution is added at a dose of about 1 mL per 1 L of the first culture medium.

Some embodiments of any of the methods described herein further include adding anti-foam to the first culture medium during culturing. Some embodiments of any of the methods described herein further include collecting the recombinant eculizumab produced in the culturing step. In some embodiments of any of the methods described herein, the collecting includes lysing the cells. In some embodiments of any of the methods described herein, the recombinant eculizumab is collected from one or both of the first culture medium and the feed culture medium.

In some embodiments of any of the methods described herein, eculizumab includes a heavy chain including or consisting of SEQ ID NO: 1 and a light chain including or consisting of SEQ ID NO: 2.

Some embodiments of any of the methods described herein further include assessing one of more cell culture parameters selected from the group of: cell growth, percentage cell viability, viable cell density, aerobic glucose consumption, eculizumab titer, specific productivity rate, volumetric productivity rate, lactate production, and eculizumab quality. Some embodiments of any of the methods described herein further include comparing the determined one or more cell culture parameters to the same one or more cell culture parameters in a large-scale eculizumab production cell culture. In some embodiments of any of the methods described herein, the large-scale eculizumab production cell culture is a 10,000 L-eculizumab production cell culture.

As used herein, the word "a" or "plurality" before a noun represents one or more of the particular noun. For example, the phrase "a mammalian cell" represents "one or more mammalian cells."

The term "processed BSA" or "processed bovine serum albumin" refers to a bovine serum albumin that has been produced by a method described herein. For example, a method used to produce a processed BSA does not include heating a solution including the serum albumin, adding a stabilizer to a solution including the serum albumin, and precipitating impurities out of a solution that includes a reconstituted lyophilized serum albumin. In some examples, the method used to produce processed BSA starts with the provision of plasma from a bovine. Non-limiting methods that can be used to produce a processed BSA are described herein.

The term "processed NZ BSA" or "processed New Zealand BSA" refers to a processed BSA as defined herein that includes a serum albumin from a bovine bred and raised in New Zealand. A non-limiting example of a processed NZ BSA is MP Biomedicals NZ BSA.

The term "eculizumab production cell culture" refers to a large-scale culture used to produce recombinant eculizumab primarily to be used for the manufacture of a pharmaceutical composition. A production cell culture can have a volume of at least 500 L, for example, about or at least 1,000 L, about or at least 2,000 L, about or at least 3,000 L, about or at least 4,000 L, about or at least 5,000 L, about or at least 6,000 L, about or at least 7,000 L, about or at least 8,000 L, about or at least 9,000 L, or about or at least 10,000 L.

The term "production bioreactor" as used herein refers to a vessel suitable for incubating a mammalian cell culture under conditions sufficient for growth of the mammalian cells in the culture and production of a recombinant protein product by the mammalian cells in the culture. Examples of production bioreactors are known in the art.

The term "mammalian cell" refers to any cell from or derived from any mammal including, for example, a human, a hamster, a mouse, a green monkey, a rat, a pig, a cow, a hamster, or a rabbit. In some embodiments, the mammalian cell can be an immortalized cell, a differentiated cell, or an undifferentiated cell.

The term "substantially free" as used herein refers to a composition (e.g., a pharmaceutical composition) that is at least or about 90% free, or about 95%, 96%, 97%, 98%, or at least or about 99% free, or about 100% free of a specific substance (e.g., contaminating proteins from a liquid culture medium or from the lysate of a mammalian cell).

The term "culturing" or "cell culturing" as used herein refers to maintenance or growth of a mammalian cell in a liquid culture medium under a controlled set of physical conditions.

The term "liquid culture medium" or "culture medium" refers to a fluid that contains sufficient nutrients to allow a mammalian cell to grow in the medium in vitro. For example, a liquid culture medium can include one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, selenium, and other necessary trace metals, and sodium bicarbonate. A liquid culture medium may include serum from a mammal. In some instances, a liquid culture medium does not contain serum or another extract from a mammal (a chemically-defined liquid culture medium). A liquid culture medium may contain trace metals, a mammalian growth hormone, and/or a mammalian growth factor. Non-limiting examples of liquid culture medium are described herein and additional examples are known in the art and are commercially available.

The term "animal-derived component free liquid culture medium" means a liquid culture medium that does not contain any components (e.g., proteins or serum) derived from an animal.

The term "serum-free liquid culture medium" refers to a liquid culture medium that does not contain animal serum.

The term "serum-added liquid culture medium" refers to a liquid culture medium that includes animal serum.

The term "chemically-defined liquid culture medium" refers to a liquid culture medium in which substantially all of the chemical components are known. For example, a chemically-defined liquid culture medium does not contain fetal bovine serum, bovine serum albumin, or human serum albumin, as these preparations typically contain a complex mix of albumins and lipids.

The term "protein-free liquid culture medium" means a liquid culture medium that does not contain any protein (e.g., any detectable protein).

"Rotary agitation" is a term well-known in the art and refers to the agitation of a culture in a bioreactor (e.g., a production bioreactor) in a generally circular fashion, e.g., clock-wise or counter-clockwise, in order to, e.g., increase the dissolved $O_2$ concentration in the culture in the bioreactor. Agitation can be performed using any method known in the art, e.g., an instrument that moves the culture in a circular or ellipsoidal motion, such as an impeller. Exemplary devices that can be used to perform rotary agitation are known in the art and are commercially available.

The term "purify" or "purifying" in certain contexts means at least partially isolating a recombinant protein from one or more other components (e.g., DNA, RNA, or other proteins) present in the liquid culture medium or cell culture lysate. The extent of purification can be specified, such as at least or about 5%, e.g., at least or about 10%, 15%, 20%, 25%, 30%, 40%, 45%, 50%, 55%, 60%, 65%, 70%, 75%, 80%, 85%, 90%, or at least or about 95% to 99.9% pure by weight. Non-limiting methods for purifying a protein from a liquid culture medium or from a mammalian cell lysate are described herein and others are known in the art.

The term "fed batch cell culture" or "fed batch culturing" means the incremental or continuous addition of a feed culture medium (e.g., liquid or solid culture medium) to an initial cell culture without substantial or significant removal of liquid culture medium from the cell culture. In some instances, the feed culture medium is the same as the first liquid culture medium present in the culture at the beginning of the culturing period. In other instances, the feed culture medium is a concentrated form of the first liquid culture medium and/or is added as a dry powder. In some examples of fed batch culture, two different feed culture media are added to the initial cell culture.

"Specific productivity rate" or "SPR" as used herein refers to the mass or enzymatic activity of a recombinant protein produced per mammalian cell per day. The SPR for a recombinant antibody is usually measured as mass/cell/day. The SPR for a recombinant enzyme is usually measured as units/cell/day or (units/mass)/cell/day.

"Volume productivity rate" or "VPR" as used herein refers to the mass or enzymatic activity of recombinant protein produced per volume of culture (e.g., per L of bioreactor, vessel, or tube volume) per day. The VPR for a recombinant antibody is usually measured as mass/L/day. The VPR for a recombinant enzyme is usually measured as units/L/day or mass/L/day.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
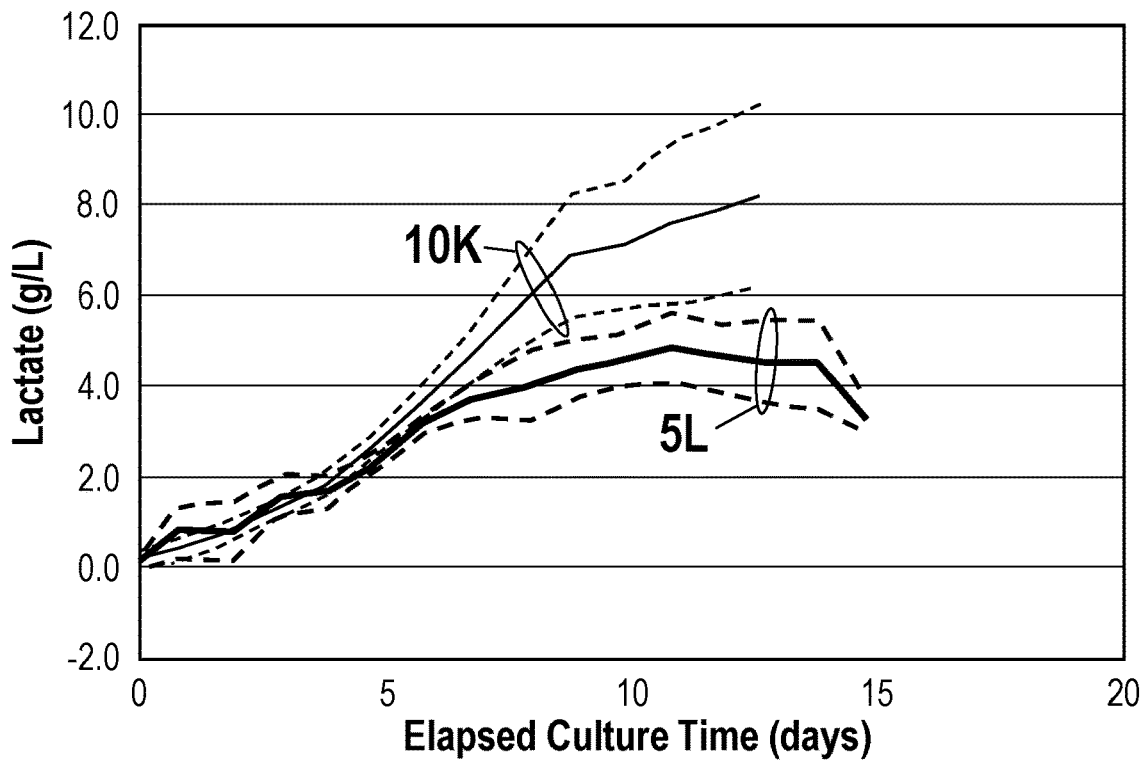
FIG. 1 is a graph showing the mean concentration (solid lines) of lactate over time in 10,000-L eculizumab production cell cultures (thin solid black lines) and previous 5-L eculizumab small scale cultures (thick solid black lines). The dashed lines represent ±1 standard deviation of the data.

Provided herein are methods of methods of replicating a large-scale eculizumab production cell culture in a small scale culture. These methods include: providing a 2-L to 25-L bioreactor (such as a fed batch bioreactor) containing a first culture medium that occupies between about 60% and about 90% of the capacity of the bioreactor and has an initial cell density of between about $2.0 \times 10^5$ and about $7.5 \times 10^5$ NS0 cells/mL, the cells containing a recombinant eculizumab-encoding nucleic acid; culturing (such as fed batch culturing) the cells in the bioreactor for at least 8 days at about 34° C. to about 39° C., at a $dO^2$ level of between about 10% to about 20%, and a rotary agitation of between about 40 RPM and about 80 RPM; maintaining (e.g., continuing) fed batch culturing until a cell density of about $10 \times 10^5$ to about $25 \times 10^5$ cells/mL is reached, then; (1) continuously adding a feed culture medium to the first culture medium for a period of about 100 hours to about 170 hours, and about 5 to 80 hours after the start of continuous addition of the feed culture medium, and (2) continuously adding an alkali base solution to the first culture medium for a period of between about 70 hours to about $10^5$ hours.

Non-limiting aspects of the methods of replicating a large-scale eculizumab production cell culture are described below. Any of the aspects described below can be used in any combination or with any other elements known in the art.

Bioreactors

A bioreactor used to culture the fed batch culture in any of the methods described herein can have a capacity of between about 2 L and about 25 L (e.g., between about 2 L and about 24 L, between about 2 L and about 22 L, between about 2 L and about 20 L, between about 2 L and about 18 L, between about 2 L and about 18 L, between about 2 L and about 16 L, between about 2 L and about 14 L, between about 2 L and about 12 L, between about 2 L and about 10 L, between about 2 L and about 9 L, between about 2 L and about 8 L, between about 2 L and about 7 L, between about 2 L and about 6 L, between about 2 L and about 5 L, between about 2 L and about 4 L, between about 2 L and about 3 L, between about 3 L and about 25 L, between about 3 L and about 24 L, between about 3 L and about 22 L, between about 3 L and about 20 L, between about 3 L and about 18 L, between about 3 L and about 16 L, between about 3 L and about 14 L, between about 3 L and about 12 L, between about 3 L and about 10 L, between about 3 L and about 9 L, between about 3 L and about 8 L, between about 3 L and about 7 L, between about 3 L and about 6 L, between about 3 L and about 5 L, between about 3 L and about 4 L, between about 4 L and about 25 L, between about 4 L and about 24 L, between about 4 L and about 22 L, between about 4 L and about 20 L, between about 4 L and about 18 L, between about 4 L and about 16 L, between about 4 L and about 14 L, between about 4 L and about 12 L, between about 4 L and about 10 L, between about 4 L and about 9 L, between about 4 L and about 8 L, between about 4 L and about 7 L, between about 4 L and about 6 L, between about 4 L and about 5 L, between about 5 L and about 25 L, between about 5 L and about 24 L, between about 5 L and about 22 L, between about 5 L and about 20 L, between about 5 L and about 18 L, between about 5 L and about 16 L, between about 5 L and about 14 L, between about 5 L and about 12 L, between about 5 L and about 10 L, between about 5 L and about 9 L, between about 5 L and about 8 L, between about 5 L and about 7 L, between about 5 L and about 6 L, between about 6 L and about 25 L, between about 6 L and about 24 L, between about 6 L and about 22 L, between about 6 L and about 20 L, between about 6 L and about 18 L, between about 6 L and about 16 L, between about 6 L and about 14 L, between about 6 L and about 12 L, between about 6 L and about 10 L, between about 6 L and about 9 L, between about 6 L and about 8 L, between about 6 L and about 7 L, between about 8 L and about 25 L, between about 8 L and about 24 L, between about 8 L and about 22 L, between about 8 L and about 20 L, between about 8 L and about 18 L, between about 8 L and about 16 L, between about 8 L and about 14 L, between about 8 L and about 12 L, between about 8 L and about 10 L, between about 8 L and about 9 L, between about 9 L and about 25 L, between about 9 L and about 24 L, between about 9 L and about 22 L, between about 9 L and about 20 L, between about 9 L and about 18 L, between about 9 L and about 16 L, between about 9 L and about 14 L, between about 9 L and about 12 L, between about 9 L and about 10 L, between about 10 L and about 25 L, between about 10 L and about 24 L, between about 10 L and about 22 L, between about 10 L and about 20 L, between about 10 L and about 18 L, between about 10 L and about 16 L, between about 10 L and about 14 L, between about 10 L and about 12 L, between about 12 L and about 25 L, between about 12 L and about 24 L, between about 12 L and about 22 L, between about 12 L and about 20 L, between about 12 L and about 18 L, between about 12 L and about 16 L, between about 12 L and about 14 L, between about 14 L and about 25 L, between about 14 L and about 24 L, between about 14 L and about 22 L, between about 14 L and about 20 L, between about 14 L and about 18 L, between about 14 L and about 16 L, between about 16 L and about 25 L, between about 16 L and about 24 L, between about 16 L and about 22 L, between about 16 L and about 20 L, between about 16 L and about 18 L, between about 18 L and about 25 L, between about 18 L and about 24 L, between about 18 L and about 22 L, between about 18 L and about 20 L, between about 20 L and about 25 L, between about 20 L and about 24 L, between about 20 L and about 22 L, or between about 22 L and about 25 L).

First Culture Medium

The methods provided herein include a step of providing a bioreactor containing a first culture medium (e.g., any of the exemplary types of culture media described herein or known in the art). The volume of the first culture medium present in the bioreactor can be between about 60% and about 90% (e.g., between about 60% and about 88%, between about 60% and about 86%, between about 60% and about 86%, between about 60% and about 84%, between about 60% and about 82%, between about 60% and about 80%, between about 60% and about 78%, between about 60% and about 76%, between about 60% and about 74%, between about 60% and about 72%, between about 60% and about 70%, between about 60% and about 68%, between about 60% and about 66%, between about 60% and about 64%, between about 62% and about 90%, between about 62% and about 88%, between about 62% and about 86%, between about 62% and about 84%, between about 62% and about 82%, between about 62% and about 80%, between about 62% and about 78%, between about 62% and about 76%, between about 62% and about 74%, between about 62% and about 72%, between about 62% and about 74%, between about 62% and about 72%, between about 62% and about 70%, between about 62% and about 68%, between about 62% and about 66%, between about 64% and about 90%, between about 64% and about 88%, between about 64% and about 86%, between about 64% and about 84%, between about 64% and about 82%, between about 64% and about 80%, between about 64% and about 78%, between about 64% and about 76%, between about 64% and about 74%, between about 64% and about 72%, between about 64% and about 70%, between about 64% and about 68%, between about 68% and about 90%, between about 68% and about 88%, between about 68% and about 86%, between about 68% and about 84%, between about 68% and about 82%, between about 68% and about 80%, between about 68% and about 78%, between about 68% and about 76%, between about 68% and about 74%, between about 68% and about 72%, between about 70% and about 90%, between about 70% and about 88%, between about 70% and about 86%, between about 70% and about 84%, between about 70% and about 82%, between about 70% and about 80%, between about 70% and about 78%, between about 70% and about 76%, between about 70% and about 74%, between about 72% and about 90%, between about 72% and about 88%, between about 72% and about 86%, between about 72% and about 84%, between about 72% and about 82%, between about 72% and about 80%, between about 72% and about 78%, between about 72% and about 76%, between about 74% and about 90%, between about 74% and about 88%, between about 74% and about 86%, between about 74% and about 84%, between about 74% and about 82%, between about 74% and about 80%, between about 74% and about 78%, between about 74% and about 76%, between about 78% and about 90%, between about 78% and about 90%, between about 78% and about 88%, between about 78% and about 86%, between about 78% and about 84%, between about 78% and about 82%, between about 80% and about 90%, between about 80% and about 88%, between about 80% and about 86%, between about 80% and about 84%, between about 82% and about 90%, between about 82% and about 88%, between about 82% and about 86%, between about 84% and about 90%, between about 84% and about 88%, or between about 86% and about 90%) of the capacity of the bioreactor.

The volume of the first culture medium present in the bioreactor can be between about 1.2 L and about 22 L (e.g., between about 1.2 L and about 20 L, between about 1.2 L and about 18 L, between about 1.2 L and about 16 L, between about 1.2 and about 14 L, between about 1.2 and about 12 L, between about 1.2 L and about 10 L, between about 1.2 L and about 9 L, between about 1.2 L and about 8 L, between about 1.2 L and about 7 L, between about 1.2 L and about 6 L, between about 1.2 L and about 5 L, between about 1.2 L and about 4 L, between about 1.2 L and about 3 L, between about 1.2 L and about 2 L, between about 2.0 L and about 22 L, between about 2.0 L and about 20 L, between about 2 L and about 18 L, between about 2 L and about 16 L, between about 2 L and about 14 L, between about 2 L and about 12 L, between about 2 L and about 10 L, between about 2 L and about 9 L, between about 2 L and about 8 L, between about 2 L and about 7 L, between about 2 L and about 6 L, between about 2 L and about 5 L, between about 2 L and about 4 L, between about 2 L and about 3 L, between about 3 L and about 22 L, between about 3 L and about 20 L, between about 3 L and about 18 L, between about 3 L and about 16 L, between about 3 L and about 14 L, between about 3 L and about 12 L, between about 3 L and about 10 L, between about 3 L and about 9 L, between about 3 L and about 8 L, between about 3 L and about 7 L, between about 3 L and about 6 L, between about 3 L and about 5 L, between about 3 L and about 4 L, between about 4 L and about 22 L, between about 4 L and about 20 L, between about 4 L and about 18 L, between about 4 L and about 16 L, between about 4 L and about 14 L, between about 4 L and about 12 L, between about 4 L and about 10 L, between about 4 L and about 9 L, between about 4 L and about 8 L, between about 4 L and about 7 L, between about 4 L and about 6 L, between about 4 L and about 5 L, between about 5 L and about 22 L, between about 5 L and about 20 L, between about 5 L and about 18 L, between about 5 L and about 16 L, between about 5 L and about 14 L, between about 5 L and about 12 L, between about 5 L and about 10 L, between about 5 L and about 9 L, between about 5 L and about 8 L, between about 5 L and about 7 L, between about 5 L and about 6 L, between about 6 L and about 22 L, between about 6 L and about 20 L, between about 6 L and about 18 L, between about 6 L and about 16 L, between about 6 L and about 14 L, between about 6 L and about 12 L, between about 6 L and about 10 L, between about 6 L and about 9 L, between about 6 L and about 8 L, between about 6 L and about 7 L, between about 7 L and about 22 L, between about 7 L and about 20 L, between about 7 L and about 18 L, between about 7 L and about 16 L, between about 7 L and about 14 L, between about 7 L and about 12 L, between about 7 L and about 10 L, between about 7 L and about 9 L, between about 7 L and about 8 L, between about 8 L and about 22 L, between about 8 L and about 20 L, between about 8 L and about 18 L, between about 8 L and about 16 L, between about 8 L and about 14 L, between about 8 L and about 12 L, between about 8 L and about 10 L, between about 8 L and about 9 L, between about 9 L and about 22 L, between about 9 L and about 20 L, between about 9 L and about 18 L, between about 9 L and about 16 L, between about 9 L and about 14 L, between about 9 L and about 12 L, between about 9 L and about 10 L, between about 10 L and about 22 L, between about 10 L and about 20 L, between about 10 L and about 18 L, between about 10 L and about 16 L, between about 10 L and about 14 L, between about 10 L and about 12 L, between about 12 L and about 22 L, between about 12 L and about 20 L, between about 12 L and about 18 L, between about 12 L and about 16 L, between about 12 L and about 14 L, between about 14 L and about 22 L, between about 14 L and about 20 L, between about 14 L and about 18 L, between about 14 L and about 16 L, between about 16 L and about 22 L, between about 16 L and about 20 L, between about 16 L and about 18 L, between about 18 L and about 22 L, between about 18 L and about 20 L, or between about 20 L and about 22 L).

NS0 Cells and Initial Cell Density

The NS0 cells used in the methods described herein can contain a recombinant nucleic acid that is stably integrated in the NS0 cell's genome and encodes a recombinant eculizumab. In some embodiments, the recombinant eculizumab is secreted by the mammalian cell into the liquid culture medium. In some instances, the cultured mammalian cells are derived from a seed culture. More particularly, the initial cell culture is the result of a seed train process or a culture from another bioreactor.

In non-limiting examples of any of the methods described herein, the cell density of mammalian cells present in the bioreactor at the start of the fed batch culturing period (initial cell density, such as initial viable cell density) is about $1.0\times10^5$ cells/mL to about $7.5\times10^5$ cells/mL, about $2.0\times10^5$ cells/mL to about $7.5\times10^5$ cells/mL, about $3.0\times10^5$ cells/mL to about $7.5\times10^5$ cells/mL, between about $4.0\times10^5$ cells/mL to about $7.5\times10^5$ cells/mL, between about $5.0\times10^5$ cells/mL to about $7.5\times10^5$ cells/mL, between about $6.0\times10^5$ cells/mL to about $7.5\times10^5$ cells/mL, between about $7.0\times10^5$ cells/mL to about $7.5\times10^6$ cells/mL, between about $1.0\times10^5$ cells/mL to about $7.0\times10^5$ cells/mL, between about $2.0\times10^5$ cells/mL to about $7.0\times10^5$ cells/mL, between about $3.0\times10^5$ cells/mL to about $7.0\times10^5$ cells/mL, between about $4.0\times10^5$ cells/mL to about $7.0\times10^5$ cells/mL, between about $5.0\times10^5$ cells/mL to about $7.0\times10^5$ cells/mL, between about $6.0\times10^5$ cells/mL to about $7.0\times10^5$ cells/mL, between about $1.0\times10^5$ cells/mL to about $6.0\times10^5$ cells/mL, between about $2.0\times10^5$ cells/mL to about $6.0\times10^5$ cells/mL, between about $3.0\times10^5$ cells/mL to about $6.0\times10^5$ cells/mL, between about $4.0\times10^5$ cells/mL to about $6.0\times10^5$ cells/mL, between about $5.0\times10^5$ cells/mL to about $6.0\times10^5$ cells/mL, between about $1.0\times10^5$ cells/mL to about $5.0\times10^5$ cells/mL, between about $2.0\times10^5$ cells/mL to about $5.0\times10^5$ cells/mL, between about $3.0\times10^5$ cells/mL to about $5.0\times10^5$ cells/mL, between about $4.0\times10^5$ cells/mL to about $5.0\times10^5$ cells/mL, between about $1.0\times10^5$ cells/mL to about $4.0\times10^5$ cells/mL, between about $2.0\times10^5$ cells/mL to about $4.0\times10^5$ cells/mL, between about $3.0\times10^5$ cells/mL to about $4.0\times10^5$ cells/mL, between about $1.0\times10^5$ cells/mL to about $3.0\times10^5$ cells/mL, between about $2.0\times10^5$ cells/mL to about $3.0\times10^5$ cells/mL, or between about $1.0\times10^5$ cells/mL to about $2.0\times10^5$ cells/mL.

Fed Batch Culturing

As is known in the art, fed batch culturing includes the incremental (periodic) or continuous addition of a feed culture medium to an initial cell culture without substantial or significant removal of the first culture medium from the cell culture. The cell culture in fed batch culturing can be disposed in a bioreactor (e.g., any of the exemplary bioreactors described herein). In some instances, the feed culture medium is the same as the first culture medium. The feed culture medium may be either in a liquid form or a dry powder. In some examples instances, the feed culture medium is a concentrated form of the first culture medium.

For example, the addition of the feed culture medium (continuously or periodically) can occur at a time point that is between 6 hours and 7 days, between about 6 hours and about 6 days, between about 6 hours and about 5 days, between about 6 hours and about 4 days, between about 6 hours and about 3 days, between about 6 hours and about 2 days, between about 6 hours and about 1 day, between about 12 hours and about 7 days, between about 12 hours and about 6 days, between about 12 hours and about 5 days, between about 12 hours and about 4 days, between about 12 hours and about 3 days, between about 12 hours and about 2 days, between about 1 day and about 7 days, between about 1 day and about 6 days, between about 1 day and about 5 days, between about 1 day and about 4 days, between about 1 day and about 3 days, between about 1 day and about 2 days, between about 2 days and about 7 days, between about 2 days and about 6 days, between about 2 days and about 5 days, between about 2 days and about 4 days, between about 2 days and about 3 days, between about 3 days and about 7 days, between about 3 days and about 6 days, between about 3 days and about 5 days, between about 3 days and about 4 days, between about 4 days and about 7 days, between about 4 days and about 6 days, between about 4 days and about 5 days, between about 5 days and about 7 days, or between about 5 days and about 6 days, after the start of the culturing period.

In some examples, two different feed culture media (e.g., any of the exemplary liquid culture media described herein) are added (continuously or incrementally) during feed batch culturing. The amount or volume of the first feed culture medium and the second feed culture medium added can be substantially the same or can differ. The first feed culture medium can be in the form of a liquid and the second feed culture medium can be in the form of a solid. In some examples, the first and the second feed culture media are liquid culture media.

The fed batch culturing can be performed for at least 8 days (e.g., 9, 10, 11, 12, 13, 14, 15, 16, 17, 18, 19, 20, 21, 22, 23, 24, or 25 days). For example, the fed batch culturing can be performed for at least 9 days, at least 10 days, at least 11 days, at least 12 days, at least 13 days, at least 14 days, at least 15 days, at least 16 days, at least 17 days, at least 18 days, at least 19 days, or at least 20 days. The feed culture medium (or first and second liquid feed culture media) can be added continuously or periodically.

Continuous Addition of a Feed Culture Medium

When the feed culture medium is added continuously, the rate of addition of the feed culture medium can be held constant or can be increased (e.g., steadily increased) over the culturing period. A continuous addition of feed culture medium can start at a specific time point during the culturing period (e.g., when the cells reach a target cell density, e.g., any of the exemplary target cell densities described herein). In some embodiments, the continuous addition of feed culture medium can be initiated at day 2, day 3, day 4, day 5, day 6, or day 7 of the culturing period. Exemplary volumes and rates of adding a feed culture medium (e.g., a first and second liquid feed culture media) to a culture are described herein.

In some embodiments a single liquid feed culture medium or a first and second liquid feed culture media are added continuously to the cell culture. The rate of addition of the single liquid feed culture medium or the rate of addition of each of the first and the second liquid feed culture medium can be between about 10 μL/minute and about 160 μL/minute (e.g., between about 10 μL/minute and about 150 μL/minute, between about 10 μL/minute and about 140 μL/minute, between about 10 μL/minute and about 130 μL/minute, between about 10 μL/minute and about 120 μL/minute, between about 10 μL/minute and about 110 μL/minute, between about 10 μL/minute and about 100 μL/minute, between about 10 μL/minute and about 90 μL/minute, between about 10 μL/minute and about 80 μL/minute, between about 10 μL/minute and about 75 μL/minute, between about 10 μL/minute and about 70 μL/minute, between about 10 μL/minute and about 65 μL/minute, between about 10 μL/minute and about 60 μL/minute, between about 10 μL/minute and about 55 μL/minute, between about 10 μL/minute and about 50 μL/minute, between about 10 μL/minute and about 45 μL/minute, between about 10 μL/minute and about 40 μL/minute, between about 10 μL/minute and about 35 μL/minute, between about 10 μL/minute and about 30 μL/minute, between about 10 μL/minute and about 25 μL/minute, between about 10 μL/minute and about 20 μL/minute, between about 10 μL/minute and about 15 μL/minute, between about 15 μL/minute and about 160 μL/minute, 15 μL/minute and about 150 μL/minute, between about 15 μL/minute and about 140 μL/minute, between about 15 μL/minute and about 130 μL/minute, between about 15 μL/minute and about 120 μL/minute, between about 15 μL/minute and about 110 μL/minute, between about 15 μL/minute and about 100 μL/minute, between about 15 μL/minute and about 90 μL/minute, between about 15 μL/minute and about 80 μL/minute, between about 15 μL/minute and about 75 μL/minute, between about 15 μL/minute and about 70 μL/minute, between about 15 μL/minute and about 65 μL/minute, between about 15 μL/minute and about 60 μL/minute, between about 15 μL/minute and about 55 μL/minute, between about 15 μL/minute and about 50 μL/minute, between about 15 μL/minute and about 45 μL/minute, between about 15 μL/minute and about 40 μL/minute, between about 15 μL/minute and about 35 μL/minute, between about 15 μL/minute and about 30 μL/minute, between about 15 μL/minute and about 25 μL/minute, between about 15 μL/minute and about 20 μL/minute, between about 20 μL/minute and about 160 μL/minute, between about 20 μL/minute and about 150 μL/minute, between about 20 μL/minute and about 140 μL/minute, between about 20 μL/minute and about 130 μL/minute, between about 20 μL/minute and about 120 μL/minute, between about 20 μL/minute and about 110 μL/minute, between about 20 μL/minute and about 100 μL/minute, between about 20 μL/minute and about 90 μL/minute, between about 20 μL/minute and about 80 μL/minute, between about 20 μL/minute and about 75 μL/minute, between about 20 μL/minute and about 70 μL/minute, between about 20 μL/minute and about 65 μL/minute, between about 20 μL/minute and about 60 μL/minute, between about 20 μL/minute and about 55 μL/minute, between about 20 μL/minute and about 50 μL/minute, between about 20 μL/minute and about 45 μL/minute, between about 20 μL/minute and about 40 μL/minute, between about 20 μL/minute and about 35 μL/minute, between about 20 μL/minute and about 30 μL/minute, between about 20 μL/minute and about 25 μL/minute, between about 30 μL/minute and about 160 μL/minute, 30 μL/minute and about 150 μL/minute, between about 30 μL/minute and about 140 μL/minute, between about 30 μL/minute and about 130 μL/minute, between about 30 μL/minute and about 120 μL/minute, between about 30 μL/minute and about 110 µL/minute, between about 30 µL/minute and about 100 µL/minute, between about 30 µL/minute and about 90 µL/minute, between about 30 µL/minute and about 80 µL/minute, between about 30 µL/minute and about 70 µL/minute, between about 30 µL/minute and about 60 µL/minute, between about 30 µL/minute and about 50 µL/minute, between about 30 µL/minute and about 40 µL/minute, between about 40 µL/minute and about 160 µL/minute, between about 40 µL/minute and about 150 µL/minute, between about 40 µL/minute and about 140 µL/minute, between about 40 µL/minute and about 130 µL/minute, between about 40 µL/minute and about 120 µL/minute, between about 40 µL/minute and about 110 µL/minute, between about 40 µL/minute and about 100 µL/minute, between about 40 µL/minute and about 90 µL/minute, between about 40 µL/minute and about 80 µL/minute, between about 40 µL/minute and about 70 µL/minute, between about 40 µL/minute and about 60 µL/minute, between about 40 µL/minute and about 50 µL/minute, between about 50 µL/minute and about 160 µL/minute, between about 50 µL/minute and about 150 µL/minute, between about 50 µL/minute and about 140 µL/minute, between about 50 µL/minute and about 130 µL/minute, between about 50 µL/minute and about 120 µL/minute, between about 50 µL/minute and about 110 µL/minute, between about 50 µL/minute and about 100 µL/minute, between about 50 µL/minute and about 90 µL/minute, between about 50 µL/minute and about 80 µL/minute, between about 50 µL/minute and about 70 µL/minute, between about 50 µL/minute and about 60 µL/minute, between about 60 µL/minute and about 160 µL/minute, between about 60 µL/minute and about 150 µL/minute, between about 60 µL/minute and about 140 µL/minute, between about 60 µL/minute and about 130 µL/minute, between about 60 µL/minute and about 120 µL/minute, between about 60 µL/minute and about 110 µL/minute, between about 60 µL/minute and about 100 µL/minute, between about 60 µL/minute and about 90 µL/minute, between about 60 µL/minute and about 80 µL/minute, between about 60 µL/minute and about 70 µL/minute, between about 70 µL/minute and about 160 µL/minute, between about 70 µL/minute and about 150 µL/minute, between about 70 µL/minute and about 140 µL/minute, between about 70 µL/minute and about 130 µL/minute, between about 70 µL/minute and about 120 µL/minute, between about 70 µL/minute and about 110 µL/minute, between about 70 µL/minute and about 100 µL/minute, between about 70 µL/minute and about 90 µL/minute, between about 70 µL/minute and about 80 µL/minute, between about 80 µL/minute and about 160 µL/minute, between about 80 µL/minute and about 150 µL/minute, between about 80 µL/minute and about 140 µL/minute, between about 80 µL/minute and about 130 µL/minute, between about 80 µL/minute and about 120 µL/minute, between about 80 µL/minute and about 110 µL/minute, between about 80 µL/minute and about 100 µL/minute, between about 80 µL/minute and about 90 µL/minute, between about 90 µL/minute and about 160 µL/minute, between about 90 µL/minute and about 150 µL/minute, between about 90 µL/minute and about 140 µL/minute, between about 90 µL/minute and about 130 µL/minute, between about 90 µL/minute and about 120 µL/minute, between about 90 µL/minute and about 110 µL/minute, between about 90 µL/minute and about 100 µL/minute, between about 100 µL/minute and about 160 µL/minute, between about 100 µL/minute and about 140 µL/minute, between about 100 µL/minute and about 120 µL/minute, between about 120 µL/minute and about 160 µL/minute, between about 120 µL/minute and about 140 µL/minute, or between about 140 µL/minute and about 160 µL/minute.

The total volume of the feed culture medium or the total volume of each of the first and the second liquid feed culture medium added to the culture over the entire culturing period can be between about 50 mL and about 2200 mL (e.g., between about 50 mL and about 2100 mL, between about 50 mL and about 2000 mL, between about 50 mL and about 1900 mL, between about 50 mL and about 1800 mL, between about 50 mL and about 1600 mL, between about 50 mL and about 1400 mL, between about 50 mL and about 1200 mL, between about 50 mL and about 1000 mL, between about 50 mL and about 800 mL, between about 50 mL and about 600 mL, between about 50 mL and about 400 mL, between about 50 mL and about 200 mL, between about 50 mL and about 190 mL, between about 50 mL and about 180 mL, between about 50 mL and about 170 mL, between about 50 mL and about 180 mL, between about 50 mL and about 170 mL, between about 50 mL and about 160 mL, between about 50 mL and about 150 mL, between about 50 mL and about 140 mL, between about 50 mL and about 130 mL, between about 50 mL and about 120 mL, between about 50 mL and about 110 mL, between about 50 mL and about 100 mL, between about 50 mL and about 90 mL, between about 50 mL and about 80 mL, between about 50 mL and about 70 mL, between about 50 mL and about 60 mL, between about 60 mL to about 2200 mL, between about 60 mL and about 2000 mL, between about 60 mL and about 1800 mL, between about 60 mL and about 1600 mL, between about 60 mL and about 1400 mL, between about 60 mL and about 1200 mL, between about 60 mL and about 1000 mL, between about 60 mL and about 800 mL, between about 60 mL and about 600 mL, between about 60 mL and about 400 mL, between about 60 mL and about 300 mL, between about 60 mL and about 200 mL, between about 60 mL and about 190 mL, between about 60 mL and about 180 mL, between about 60 mL and about 170 mL, between about 60 mL and about 160 mL, between about 60 mL and about 150 mL, between about 60 mL and about 140 mL, between about 60 mL and about 130 mL, between about 60 mL and about 120 mL, between about 60 mL and about 110 mL, between about 60 mL and about 100 mL, between about 60 mL and about 90 mL, between about 60 mL and about 80 mL, between about 60 mL and about 70 mL, between about 80 mL and about 2200 mL, between about 80 mL and about 2000 mL, between about 80 mL and about 1800 mL, between about 80 mL and about 1600 mL, between about 80 mL and about 1400 mL, between about 80 mL and about 1200 mL, between about 80 mL and about 1000 mL, between about 80 mL and about 800 mL, between about 80 mL and about 600 mL, between about 80 mL and about 400 mL, between about 80 mL and about 300 mL, between about 80 mL and about 200 mL, between about 80 mL and about 190 mL, between about 80 mL and about 180 mL, between about 80 mL and about 170 mL, between about 80 mL and about 160 mL, between about 80 mL and about 150 mL, between about 80 mL and about 140 mL, between about 80 mL and about 130 mL, between about 80 mL and about 120 mL, between about 80 mL and about 110 mL, between about 80 mL and about 100 mL, between about 80 mL and about 90 mL, between about 100 mL and about 2200 mL, between about 100 mL and about 2000 mL, between about 100 mL and about 1800 mL, between about 100 mL and about 1600 mL, between about 100 mL and about 1400 mL, between about 100 mL and about 1200 mL, between about 100 mL and about 1000 mL, between about 100 mL and about 800 mL, between about 100 mL and about 600 mL, between about 100 mL and about 400 mL, between about 100 mL and about 300 mL, between about 100 mL and about 200 mL, between about 100 mL and about 190 mL, between about 100 mL and about 180 mL, between about 100 mL and about 170 mL, between about 100 mL and about 160 mL, between about 100 mL and about 150 mL, between about 100 mL and about 140 mL, between about 100 mL and about 130 mL, between about 100 mL and about 120 mL, between about 100 mL and about 110 mL, between about 120 mL and about 2200 mL, between about 120 mL and about 2000 mL, between about 120 mL and about 1800 mL, between about 120 mL and about 1600 mL, between about 120 mL and about 1400 mL, between about 120 mL and about 1200 mL, between about 120 mL and about 1000 mL, between about 120 mL and about 800 mL, between about 120 mL and about 600 mL, between about 120 mL and about 400 mL, between about 120 mL and about 300 mL, between about 120 mL and about 200 mL, between about 120 mL and about 190 mL, between about 120 mL and about 180 mL, between about 120 mL and about 170 mL, between about 120 mL and about 160 mL, between about 120 mL and 150 mL, between about 120 mL and about 140 mL, between about 120 mL and about 130 mL, between about 140 mL and about 2200 mL, between about 140 mL and about 2000 mL, between about 140 mL and about 1800 mL, between about 140 mL and about 1600 mL, between about 140 mL and about 1400 mL, between about 140 mL and about 1200 mL, between about 140 mL and about 1000 mL, between about 140 mL and about 800 mL, between about 140 mL and about 600 mL, between about 140 mL and about 400 mL, between about 140 mL and about 300 mL, between about 140 mL and about 200 mL, between about 140 mL and about 190 mL, between about 140 mL and about 180 mL, between about 140 mL and about 170 mL, between about 140 mL and about 160 mL, between about 140 mL and about 150 mL, between about 160 mL and about 2200 mL, between about 160 mL and about 2000 mL, between about 160 mL and about 1800 mL, between about 160 mL and about 1600 mL, between about 160 mL and about 1400 mL, between about 160 mL and about 1200 mL, between about 160 mL and about 1000 mL, between about 160 mL and about 800 mL, between about 160 mL and about 600 mL, between about 160 mL and about 500 mL, between about 160 mL and about 400 mL, between about 160 mL and about 300 mL, between about 160 mL and about 200 mL, between about 160 mL and about 190 mL, between about 160 mL and about 180 mL, between about 160 mL and about 170 mL, between about 180 mL and about 2200 mL, between about 180 mL and about 2000 mL, between about 180 mL and about 1800 mL, between about 180 mL and about 1600 mL, between about 180 mL and about 1400 mL, between about 180 mL and about 1400 mL, between about 180 mL and about 1200 mL, between about 180 mL and about 1000 mL, between about 180 mL and about 800 mL, between about 180 mL and about 600 mL, between about 180 mL and about 400 mL, between about 180 mL and about 300 mL, between about 180 mL and about 200 mL, between about 180 mL and about 190 mL, between about 200 mL and about 2200 mL, between about 200 mL and about 2000 mL, between about 200 mL and about 1800 mL, between about 200 mL and about 1600 mL, between about 200 mL and about 1400 mL, between about 200 mL and about 1200 mL, between about 200 mL and about 1000 mL, between about 200 mL and about 800 mL, between about 200 mL and about 600 mL, between about 200 mL and about 400 mL, between about 400 mL and about 2200 mL, between about 400 mL and about 2000 mL, between about 400 mL and about 1800 mL, between about 400 mL and about 1600 mL, between about 400 mL and about 1400 mL, between about 400 mL and about 1200 mL, 400 mL and about 1000 mL, between about 400 mL and about 800 mL, between about 400 mL and about 600 mL, between about 600 mL and about 2200 mL, between about 600 mL and about 2000 mL, between about 600 mL and about 1800 mL, between about 600 mL and about 1600 mL, between about 600 mL and about 1400 mL, between about 600 mL and about 1200 mL, between about 600 mL and about 1000 mL, between about 600 mL and about 800 mL, between about 800 mL and about 2200 mL, between about 800 mL and about 2000 mL, between about 800 mL and about 1800 mL, between about 800 mL and about 1600 mL, between about 800 mL and about 1400 mL, between about 800 mL and about 1200 mL, between about 800 mL and about 1000 mL, between about 1000 mL and about 2200 mL, between about 1000 mL and about 2000 mL, between about 1000 mL and about 1800 mL, between about 1000 mL and about 1600 mL, between about 1000 mL and about 1400 mL, between about 1000 mL and about 1200 mL, between about 1200 mL and about 2200 mL, between about 1200 mL and about 2000 mL, between about 1200 mL and about 1800 mL, between about 1200 mL and about 1600 mL, between about 1200 mL and about 1400 mL, between about 1400 mL and about 2200 mL, between about 1400 mL and about 2000 mL, between about 1400 mL and about 1800 mL, between about 1400 mL and about 1600 mL, between about 1600 mL and about 2200 mL, between about 1600 mL and about 2000 mL, between about 1600 mL and about 1800 mL, between about 1800 mL and about 2200 mL, between about 1800 mL and about 2000 mL, or between about 2000 mL and about 2200 mL.

The total volume of the feed culture medium or the total volume of each of the first and the second liquid feed culture medium added to the culture over the entire culturing period can be between about 1% and about 15% (e.g., about 1% and about 14%, between about 1% and about 13%, between about 1% and about 12%, between about 1% and about 11%, between about 1% and about 10%, between about 1% and about 9%, between about 1% and about 8%, between about 1% and about 7%, between about 1% and about 6%, between about 1% and about 5%, between about 1% and about 4%, between about 1% and about 3%, between about 1% and about 2%, between about 2% and about 15%, between about 2% and about 13%, between about 2% and about 12%, between about 2% and about 11%, between about 2% and about 10%, between about 2% and about 9%, between about 2% and about 8%, between about 2% and about 7%, between about 2% and about 6%, between about 2% and about 5%, between about 2% and about 4%, between about 2% and about 3%, between about 3% and about 15%, between about 3% and about 14%, between about 3% and about 13%, between about 3% and about 12%, between about 3% and about 11%, between about 3% and about 10%, between about 3% and about 9%, between about 3% and about 8%, between about 3% and about 7%, between about 3% and about 6%, between about 3% and about 5%, between about 3% and about 4%, between about 4% and about 15%, between about 4% and about 14%, between about 4% and about 13%, between about 4% and about 12%, between about 4% and about 11%, between about 4% and about 10%, between about 4% and about 9%, between about 4% and about 8%, between about 4% and about 7%, between about 4% and about 6%, between about 4% and about 5%, between about 5% and about 15%, between about 5% and about 14%, between about 5% and about 13%, between about 5% and about 12%, between about 5% and about 11%, between about 5% and about 10%, between about 5% and about 9%, between about 5% and about 8%, between about 5% and about 7%, between about 5% and about 6%, between about 6% and about 15%, between about 6% and about 14%, between about 6% and about 13%, between about 6% and about 12%, between about 6% and about 11%, between about 6% and about 10%, between about 6% and about 9%, between about 6% and about 8%, between about 6% and about 7%, between about 7% and about 15%, between about 7% and about 14%, between about 7% and about 13%, between about 7% and about 12%, between about 7% and about 11%, between about 7% and about 10%, between about 7% and about 9%, between about 7% and about 8%, between about 8% and about 15%, between about 8% and about 14%, between about 8% and about 13%, between about 8% and about 12%, between about 8% and about 11%, between about 8% and about 10%, between about 8% and about 9%, between about 9% and about 15%, between about 9% and about 14%, between about 9% and about 13%, between about 9% and about 12%, between about 9% and about 11%, between about 9% and about 10%, between about 10% and about 15%, between about 10% and about 14%, between about 10% and about 13%, between about 10% and about 12%, between about 10% and about 11%, between about 11% and about 15%, between about 11% and about 14%, between about 11% and about 13%, between about 11% and about 12%, between about 12% and about 15%, between about 12% and about 14%, between about 12% and about 13%, between about 13% and about 15%, between about 13% and about 14%, or between about 14% and about 15) of the volume of the first culture medium or the volume of the culture following inoculation but before the addition of fed culture medium.

The continuous addition of the feed culture medium or the continuous addition of the first and second feed culture media can take place over a period of between about 20 hours to about 200 hours (e.g., between about 20 hours to about 190 hours, between about 20 hours to about 180 hours, between about 20 hours to about 170 hours, between about 20 hours to about 160 hours, between about 20 hours to about 150 hours, between about 20 hours to about 140 hours, between about 20 hours to about 130 hours, between about 20 hours to about 120 hours, between about 20 hours to about 110 hours, between about 20 hours to about 100 hours, between about 20 hours to about 90 hours, between about 20 hours to about 80 hours, between about 20 hours to about 70 hours, between about 20 hours to about 60 hours, between about 20 hours to about 50 hours, between about 20 hours to about 40 hours, between about 20 hours to about 30 hours, between about 30 hours to about 200 hours, between about 30 hours to about 190 hours, between about 30 hours to 180 hours, between about 30 hours to about 170 hours, between about 30 hours to about 160 hours, between about 30 hours to about 150 hours, between about 30 hours to about 140 hours, between about 30 hours to about 130 hours, between about 30 hours to about 120 hours, between about 30 hours to about 110 hours, between about 30 hours to about 100 hours, between about 30 hours to about 90 hours, between about 30 hours to about 80 hours, between about 30 hours to about 70 hours, between about 30 hours to about 60 hours, between about 30 hours to about 50 hours, between about 30 hours to about 40 hours, between about 40 hours to about 200 hours, between about 40 hours to about 190 hours, between about 40 hours to about 180 hours, between 40 hours to about 170 hours, between about 40 hours to about 160 hours, between about 40 hours to about 150 hours, between about 40 hours to about 140 hours, between about 40 hours to about 130 hours, between about 40 hours to about 120 hours, between about 40 hours to about 110 hours, between 40 hours to about 100 hours, between 40 hours to about 90 hours, between 40 hours to about 80 hours, between about 40 hours to about 70 hours, between about 40 hours to about 60 hours, between about 40 hours to about 50 hours, between about 50 hours to about 200 hours, between about 50 hours to about 190 hours, between about 50 hours to about 180 hours, between about 50 hours to about 170 hours, between about 50 hours to about 160 hours, between about 50 hours to about 150 hours, between about 50 hours to about 140 hours, between about 50 hours to about 130 hours, between about 50 hours to about 120 hours, between about 50 hours to about 110 hours, between about 50 hours to about 100 hours, between about 50 hours to about 90 hours, between about 50 hours to about 80 hours, between about 50 hours to about 70 hours, between about 50 hours to about 60 hours, between about 60 hours to about 200 hours, between about 60 hours to about 190 hours, between about 60 hours to about 180 hours, between about 60 hours to about 170 hours, between about 60 hours to about 160 hours, between about 60 hours to about 150 hours, between about 60 hours to about 140 hours, between about 60 hours to about 130 hours, between about 60 hours to about 120 hours, between about 60 hours to about 110 hours, between about 60 hours to about 100 hours, between about 60 hours to about 90 hours, between about 60 hours to about 80 hours, between about 60 hours to about 70 hours, between about 70 hours to about 200 hours, between about 70 hours to about 190 hours, between about 70 hours to about 180 hours, between about 70 hours to about 170 hours, between about 70 hours to about 160 hours, between about 70 hours to about 150 hours, between about 70 hours to about 140 hours, between about 70 hours to about 130 hours, between about 70 hours to about 120 hours, between about 70 hours to about 110 hours, between about 70 hours to about 100 hours, between about 70 hours to about 90 hours, between about 70 hours to about 80 hours, between about 80 hours to about 200 hours, between about 80 hours to about 190 hours, between about 80 hours to about 180 hours, between about 80 hours to about 170 hours, between about 80 hours to about 160 hours, between about 80 hours to about 150 hours, between about 80 hours to about 140 hours, between about 80 hours to about 130 hours, between about 80 hours to about 120 hours, between about 80 hours to about 110 hours, between about 80 hours to about 100 hours, between about 80 hour to about 90 hours, between about 90 hours to about 200 hours, between about 90 hours to about 190 hours, between 90 hours to about 180 hours, between about 90 hours to about 180 hours, between about 90 hours to about 170 hours, between about 90 hours to about 160 hours, between about 90 hours to about 150 hours, between about 90 hours to about 140 hours, between about 90 hours to about 130 hours, between about 90 hours to about 120 hours, between about 90 hours to about 110 hours, between about 90 hours to about 100 hours, between about 100 hours to about 200 hours, between about 100 hours to about 190 hours, between about 100 hours to about 180 hours, between about 100 hours to about 170 hours, between about 100 hours to about 160 hours, between about 100 hours to about 150 hours, between about 100 hours to about 140 hours, between about 100 hours to about 130 hours, between about 100 hours to about 120 hours, between about 100 hours to about 110 hours, between about 110 hours to about 200 hours, between about 110 hours to about 190 hours, between about 110 hours to about 180 hours, between about 110 hours to about 170 hours, between about 110 hours to about 160 hours, between about 110 hours to about 150 hours, between about 110 hours to about 140 hours, between about 110 hours to about 130 hours, between about 110 hours to about 120 hours, between about 120 hours to about 200 hours, between about 120 hours to about 190 hours, between about 120 hours to about 180 hours, between about 120 hours to about 170 hours, between about 120 hours to about 160 hours, between about 120 hours to about 150 hours, between about 120 hours to about 140 hours, between about 120 hours to about 130 hours, between about 130 hours to about 200 hours, between about 130 hours to about 190 hours, between about 130 hours to about 180 hours, between about 130 hours to about 170 hours, between about 130 hours to about 160 hours, between about 130 hours to about 150 hours, between about 130 hours to about 140 hours, between about 130 hours to about 135 hours, between about 140 hours to about 200 hours, between about 140 hours to about 190 hours, between about 140 hours to about 180 hours, between about 140 hours to about 170 hours, between about 140 hours to about 160 hours, between about 140 hours to about 150 hours, between about 150 hours to about 200 hours, between about 150 hours to about 190 hours, between about 150 hours to about 180 hours, between about 150 hours to about 170 hours, between about 150 hours to about 160 hours, between about 160 hours to about 200 hours, between about 160 hours to about 190 hours, between about 160 hours to about 180 hours, between about 160 hours to about 170 hours, between about 170 hours to about 200 hours, between about 170 hours to about 190 hours, between about 170 hours to about 180 hours, between about 180 hours to about 200 hours, between about 180 hours to about 190 hours, or between about 190 hours to about 200 hours.

The continuous addition of the feed culture medium or the continuous addition of both the first and the second feed culture media can be initiated at, e.g., at day 1, day 2, day 3, day 4, day 5, day 6, day 7, or day 8 of the fed batch culture. The continuous addition of the feed culture medium or the continuous addition of both the first and the second feed culture media is initiated when the culture reaches a target cell density of, e.g., about $1.0 \times 10^6$ cells/mL, about $1.1 \times 10^6$ cells/mL, about $1.2 \times 10^6$ cells/mL, about $1.3 \times 10^6$ cells/mL, about $1.4 \times 10^6$ cells/mL, about $1.5 \times 10^6$ cells/mL, about $1.6 \times 10^6$ cells/mL, about $1.7 \times 10^6$ cells/mL, about $1.8 \times 10^6$ cells/mL, about $1.9 \times 10^6$ cells/mL, about $2.0 \times 10^6$ cells/mL, about $2.1 \times 10^6$ cells/mL, about $2.2 \times 10^6$ cells/mL, about $2.3 \times 10^6$ cells/mL, about $2.4 \times 10^6$ cells/mL, about $2.5 \times 10^6$ cells/mL, between about $1.0 \times 10^6$ cells/mL and about $2.5 \times 10^6$ cells/mL, between about $1.0 \times 10^6$ cells/mL and about $2.4 \times 10^6$ cells/mL, between about $1.0 \times 10^6$ cells/mL and about $2.3 \times 10^6$ cells/mL, between about $1.0 \times 10^6$ cells/mL and about $2.2 \times 10^6$ cells/mL, between about $1.0 \times 10^6$ cells/mL and about $2.1 \times 10^6$ cells/mL, between about $1.0 \times 10^6$ cells/mL and about $2.0 \times 10^6$ cells/mL, between about $1.0 \times 10^6$ cells/mL and about $1.9 \times 10^6$ cells/mL, between about $1.0 \times 10^6$ cells/mL and about $1.8 \times 10^6$ cells/mL, between about $1.0 \times 10^6$ cells/mL and about $1.7 \times 10^6$ cells/mL, between about $1.0 \times 10^6$ cells/mL and about $1.6 \times 10^6$ cells/mL, between about $1.0 \times 10^6$ cells/mL and about $1.5 \times 10^6$ cells/mL, between about $1.0 \times 10^6$ cells/mL and about $1.4 \times 10^6$ cells/mL, between about $1.0 \times 10^6$ cells/mL and about $1.3 \times 10^6$ cells/mL, between about $1.0 \times 10^6$ cells/mL and about $1.2 \times 10^6$ cells/mL, between about $1.1 \times 10^6$ cells/mL and about $2.5 \times 10^6$ cells/mL, between about $1.1 \times 10^6$ cells/mL and about $2.4 \times 10^6$ cells/mL, between about $1.1 \times 10^6$ cells/mL and about $2.3 \times 10^6$ cells/mL, between about $1.1 \times 10^6$ cells/mL and about $2.2 \times 10^6$ cells/L, between about $1.1 \times 10^6$ cells/mL and about $2.1 \times 10^6$ cells/mL, between about $1.1 \times 10^6$ cells/mL and about $2.0 \times 10^6$ cells/mL, between about $1.1 \times 10^6$ cells/mL and about $1.9 \times 10^6$ cells/mL, between about $1.1 \times 10^6$ cells/mL and about $1.8 \times 10^6$ cells/mL, between about $1.1 \times 10^6$ cells/mL and about $1.7 \times 10^6$ cells/mL, between about $1.1 \times 10^6$ cells/mL and about $1.6 \times 10^6$ cells/mL, between about $1.1 \times 10^6$ cells/mL and about $1.5 \times 10^6$ cells/mL, between about $1.1 \times 10^6$ cells/mL and about $1.4 \times 10^6$ cells/mL, between about $1.1 \times 10^6$ cells/mL and about $1.3 \times 10^6$ cells/mL, between about $1.2 \times 10^6$ cells/mL and about $2.5 \times 10^6$ cells/mL, between about $1.2 \times 10^6$ cells/mL and about $2.4 \times 10^6$ cells/mL, between about $1.2 \times 10^6$ cells/mL and about $2.3 \times 10^6$ cells/mL, between about $1.2 \times 10^6$ cells/mL and about $2.2 \times 10^6$ cells/mL, between about $1.2 \times 10^6$ cells/mL and about $2.1 \times 10^6$ cells/mL, between about $1.2 \times 10^6$ cells/mL and about $2.0 \times 10^6$ cells/mL, between about $1.2 \times 10^6$ cells/mL and about $1.9 \times 10^6$ cells/mL, between about $1.2 \times 10^6$ cells/mL and about $1.8 \times 10^6$ cells/mL, between about $1.2 \times 10^6$ cells/mL and about $1.7 \times 10^6$ cells/mL, between about $1.2 \times 10^6$ cells/mL and about $1.6 \times 10^6$ cells/mL, between about $1.2 \times 10^6$ cells/mL and about $1.5 \times 10^6$ cells/mL, between about $1.2 \times 10^6$ cells/mL and about $1.4 \times 10^6$ cells/mL, between about $1.3 \times 10^6$ cells/mL and about $2.5 \times 10^6$ cells/mL, between about $1.3 \times 10^6$ cells/mL and about $2.4 \times 10^6$ cells/mL, between about $1.3 \times 10^6$ cells/mL and about $2.3 \times 10^6$ cells/mL, between about $1.3 \times 10^6$ cells/mL and about $2.2 \times 10^6$ cells/mL, between about $1.3 \times 10^6$ cells/mL and about $2.1 \times 10^6$ cells/mL, $1.3 \times 10^6$ cells/mL and about $2.0 \times 10^6$ cells/mL, between about $1.3 \times 10^6$ cells/mL and about $1.9 \times 10^6$ cells/mL, between about $1.3 \times 10^6$ cells/mL and about $1.8 \times 10^6$ cells/mL, between about $1.3 \times 10^6$ cells/mL and about $1.7 \times 10^6$ cells/mL, between about $1.3 \times 10^6$ cells/mL and about $1.6 \times 10^6$ cells/mL, $1.3 \times 10^6$ cells/mL and about $1.5 \times 10^6$ cells/mL, between about $1.4 \times 10^6$ cells/mL and about $2.5 \times 10^6$ cells/mL, between about $1.4 \times 10^6$ cells/mL and about $2.4 \times 10^6$ cells/mL, between about $1.4 \times 10^6$ cells/mL and about $2.3 \times 10^6$ cells/mL, between about $1.4 \times 10^6$ cells/mL and about $2.2 \times 10^6$ cells/mL, $1.4 \times 10^6$ cells/mL and about $2.1 \times 10^6$ cells/mL, between about $1.4 \times 10^6$ cells/mL and about $2.0 \times 10^6$ cells/mL, between about $1.4 \times 10^6$ cells/mL and about $1.9 \times 10^6$ cells/mL, between about $1.4 \times 10^6$ cells/mL and about $1.8 \times 10^6$ cells/mL, between about $1.4 \times 10^6$ cells/mL and about $1.7 \times 10^6$ cells/mL, between about $1.4 \times 10^6$ cells/mL and about $1.6 \times 10^6$ cells/mL, between about $1.5 \times 10^6$ cells/mL and about $2.5 \times 10^6$ cells/mL, between about $1.5 \times 10^6$ cells/mL and about $2.4 \times 10^6$ cells/mL, between about $1.5 \times 10^6$ cells/mL and about $2.3 \times 10^6$ cells/mL, between about $1.5 \times 10^6$ cells/mL and about $2.2 \times 10^6$ cells/mL, $1.5 \times 10^6$ cells/mL and about $2.1 \times 10^6$ cells/mL, between about $1.5 \times 10^6$ cells/mL and about $2.0 \times 10^6$ cells/mL, between about $1.5 \times 10^6$ cells/mL and about $1.9 \times 10^6$ cells/mL, between about $1.5 \times 10^6$ cells/mL and about $1.8 \times 10^6$ cells/mL, between about $1.5 \times 10^6$ cells/mL and about $1.7 \times 10^6$ cells/mL, between about $1.6 \times 10^6$ cells/mL and about $2.5 \times 10^6$ cells/mL, between about $1.6 \times 10^6$ cells/mL and about $2.4 \times 10^6$ cells/mL, between about $1.6 \times 10^6$ cells/mL and about $2.3 \times 10^6$ cells/mL, between about $1.6 \times 10^6$ cells/mL and about $2.2 \times 10^6$ cells/mL, $1.6 \times 10^6$ cells/mL and about $2.1 \times 10^6$ cells/mL, between about $1.6 \times 10^6$ cells/mL and about $2.0 \times 10^6$ cells/mL, between about $1.6 \times 10^6$ cells/mL and about $1.9 \times 10^6$ cells/mL, between about $1.6 \times 10^6$ cells/mL and about $1.8 \times 10^6$ cells/mL, between about $1.7 \times 10^6$ cells/mL and about $2.5 \times 10^6$ cells/mL, between about $1.7 \times 10^6$ cells/mL and about $2.4 \times 10^6$ cells/mL, between about $1.7 \times 10^6$ cells/mL and about $2.3 \times 10^6$ cells/mL, between about $1.7 \times 10^6$ cells/mL and about $2.2 \times 10^6$ cells/mL, $1.7 \times 10^6$ cells/mL and about $2.1 \times 10^6$ cells/mL, between about $1.7 \times 10^6$ cells/mL and about $2.0 \times 10^6$ cells/mL, between about $1.7 \times 10^6$ cells/mL and about $1.9 \times 10^6$ cells/mL, between about $1.8 \times 10^6$ cells/mL and about $2.5 \times 10^6$ cells/mL, between about $1.8 \times 10^6$ cells/mL and about $2.4 \times 10^6$ cells/mL, between about $1.8 \times 10^6$ cells/mL and about $2.3 \times 10^6$ cells/mL, between about $1.8 \times 10^6$ cells/mL and about $2.2 \times 10^6$ cells/mL, $1.8 \times 10^6$ cells/mL and about $2.1 \times 10^6$ cells/mL, between about $1.8 \times 10^6$ cells/mL and about $2.0 \times 10^6$ cells/mL, between about $1.9 \times 10^6$ cells/mL and about $2.5 \times 10^6$ cells/mL, between about $1.9 \times 10^6$ cells/mL and about $2.4 \times 10^6$ cells/mL, between about $1.9 \times 10^6$ cells/mL and about $2.3 \times 10^6$ cells/mL, between about $1.9 \times 10^6$ cells/mL and about $2.2 \times 10^6$ cells/mL, $1.9 \times 10^6$ cells/mL and about $2.1 \times 10^6$ cells/mL, between about $2.0 \times 10^6$ cells/mL and about $2.5 \times 10^6$ cells/mL, between about $2.0 \times 10^6$ cells/mL and about $2.4 \times 10^6$ cells/mL, between about $2.0 \times 10^6$ cells/mL and about $2.3 \times 10^6$ cells/mL, between about $2.0 \times 10^6$ cells/mL and about $2.2 \times 10^6$ cells/mL, between about $2.1 \times 10^6$ cells/mL and about $2.5 \times 10^6$ cells/mL, between about $2.1 \times 10^6$ cells/mL and about $2.4 \times 10^6$ cells/mL, between about $2.1 \times 10^6$ cells/mL and about $2.3 \times 10^6$ cells/mL, between about $2.2 \times 10^6$ cells/mL and about $2.5 \times 10^6$ cells/mL, between about $2.2 \times 10^6$ cells/mL and about $2.4 \times 10^6$ cells/mL, or between about $2.3 \times 10^6$ cells/mL and about $2.5 \times 10^6$ cells/mL.

In some embodiments of any of the methods described herein, the continuous addition of the first and second liquid feed culture media starts at the same time and the flow rate, the total volume added over the culturing period, and the length of time of addition for each of the first and the second liquid feed culture media are the same or substantially the same.

Periodic Addition of Feed Culture Medium

In some embodiments, an incremental (periodic) addition of feed culture medium can begin when the mammalian cells reach a target cell density (e.g., any of the exemplary target cell densities described herein). Incremental feed culture media addition can occur at a regular intervals (e.g., every day, every other day, or every third day) or can occur when the cells reach specific target cell densities (e.g., target cell densities that increase over the culturing period). In some embodiments, the amount of feed culture medium added can progressively increase between the first incremental addition of feed culture medium and subsequent additions of feed culture medium. The total volume of feed culture medium added to the culture over the culturing period can be any of the exemplary total volumes of feed culture medium described herein.

Culture Media

Liquid culture media that can be used in the culturing step are known in the art. The liquid culture medium (e.g., the first culture medium and/or the feed culture medium, and one or more of the first culture medium, the first feed culture medium, and the second feed culture medium) can be supplemented with a mammalian serum (e.g., fetal calf serum or bovine serum, e.g., New Zealand bovine serum), and/or a growth hormone or growth factor (e.g., insulin, transferrin, or epidermal growth factor). Alternatively or in addition, the liquid culture medium (e.g., the first culture medium and/or the feed culture medium, and one or more of the first culture medium, the first feed culture medium, and the second feed culture medium) can be a chemically-defined liquid culture medium, an animal-derived component-free liquid culture medium, a serum-free liquid culture medium, or a serum-containing liquid culture medium. The liquid culture medium (e.g., the first culture medium and/or the feed culture medium, and one or more of the first culture medium, the first feed culture medium, and the second feed culture medium) can include, e.g., a processed bovine serum albumin. Non-limiting examples of chemically-defined liquid culture media, animal-derived component free liquid culture media, serum-free liquid culture media, and serum-containing liquid culture media are commercially available.

A liquid culture medium typically contains an energy source (e.g., a carbohydrate, such as glucose), essential amino acids (e.g., the basic set of twenty amino acids plus cysteine), vitamins and/or other organic compounds required at low concentrations, free fatty acids, and/or trace elements. The liquid culture medium can, if desired, be supplemented with, e.g., a mammalian hormone or growth factor (e.g., insulin, transferrin, or epidermal growth factor), salts and buffers (e.g., calcium, magnesium, and phosphate salts), nucleosides and bases (e.g., adenosine, thymidine, and hypoxanthine), protein and tissue hydrolysates, and/or any combination of these or other additives.

Non-limiting examples of liquid culture media that can be useful in the presently described methods include, e.g., CD CHO, Opti CHO, and Forti CHO (all available from Life Technologies; Grand Island, N.Y.), Hycell CHO medium (Thermo Fisher Scientific, Inc.; Waltham, Mass.), Ex-cell CD CHO Fusion medium (Sigma-Aldrich Co.; St. Louis, Mo.), and PowerCHO medium (Lonza Group, Ltd.; Basel, Switzerland). Medium components that also may be useful in the present methods include, but are not limited to, chemically-defined (CD) hydrolysates, e.g., CD peptone, CD polypeptides (two or more amino acids), and CD growth factors. Additional examples of liquid culture media and medium components are known in the art.

The culture media used in the culturing of the mammalian cells can have a pH of between about 6.5 and about 7.5 (e.g., between about 6.5 and about 7.4, between about 6.5 and about 7.3, between about 6.5 and about 7.2, between about 6.5 and about 7.1, between about 6.5 and about 7.0, between about 6.5 and about 6.9, between about 6.5 and about 6.8, between about 6.5 and about 6.7, between about 6.6 and about 7.5, between about 6.6 and about 7.4, between about 6.6 and about 7.3, between about 6.6 and about 7.2, between about 6.6 and about 7.1, between about 6.6 and about 7.0, between about 6.6 and about 6.9, between about 6.6 and about 6.8, between about 6.7 and about 7.5, between about 6.7 and about 7.4, between about 6.7 and about 7.3, between about 6.7 and about 7.2, between about 6.7 and about 7.1, between about 6.7 and about 7.0, between about 6.7 and about 6.9, between about 6.8 and about 7.5, between about 6.8 and about 7.4, between about 6.8 and about 7.3, between about 6.8 and about 7.2, between about 6.8 and about 7.1, between about 6.8 and about 7.0, between about 6.9 and about 7.5, between about 6.9 and about 7.4, between about 6.9 and about 7.3, between about 6.9 and about 7.2, between about 6.9 and about 7.1, between about 7.0 and about 7.5, between about 7.0 and about 7.4, between about 7.0 and about 7.3, between about 7.0 and about 7.2, between about 7.1 and about 7.5, between about 7.1 and about 7.4, between about 7.1 and about 7.3, between about 7.2 and about 7.5, between about 7.2 and about 7.4, or between about 7.3 and about 7.5).

Skilled practitioners will appreciate that the liquid culture medium used in culturing can be the same or can change during the culturing period (e.g., the first culture medium and the feed culture medium or the first culture medium and the first and/or second feed culture medium can be the same type of media or different type of media).

In some embodiments, the culture media added to a fed batch culture can be a solid composition. Examples of solid culture media that can be added to a fed batch culture are known in the art.

Any of the culture media used in the methods described herein can include a processed BSA. A processed BSA is a bovine serum albumin that has been produced by a method described herein. For example, a method for producing a processed BSA does not include heating a solution including the serum albumin, adding a stabilizer to a solution including the serum albumin, and precipitating impurities out of a solution that includes a reconstituted lyophilized serum albumin. A method for producing a processed BSA can start with a step of providing plasma from a bovine. A processed BSA can be a BSA produced by a method that includes, for example, the steps of providing plasma from a bovine, desalting the plasma, filtering the plasma using ultrafiltration, precipitating euglobulin out of the plasma, filtering the plasma to remove the precipitated euglobulin, performing ion exchange chromatography on the plasma to provide an eluate comprising serum albumin and immunoglobulins, precipitating immunoglobulins out of the eluate using ammonium sulfate precipitation, removing the precipitated immunoglobulins from the eluate, concentrating and freeze-drying the eluate to produce a lyophilized material comprising serum albumin, and optionally reconstituting the lyophilized material into a solution. A non-limiting example of a processed BSA is MP Biomedicals NZ BSA.

Any of the culture media used in any of the methods described herein can include 0.1 g/L or more (e.g., at least 0.2 g/L, at least 0.3 g/L, at least 0.4 g/L, at least 0.5 g/L, at least 0.6 g/L, at least 0.7 g/L, at least 0.8 g/L, at least 0.9 g/L, at least 1.0 g/L, at least 1.1 g/L, at least 1.2 g/L, at least 1.3 g/L, at least 1.4 g/L, at least 1.5 g/L, at least 1.6 g/L, at least 1.7 g/L, at least 1.8 g/L, at least 1.9 g/L, at least 2.0 g/L, at least 2.1 g/L, at least 2.2 g/L, at least 2.3 g/L, at least 2.4 g/L, at least 2.5 g/L, at least 2.6 g/L, at least 2.7 g/L, at least 2.8 g/L, at least 2.9 g/L, or at least 3.0 g/L) processed BSA (such as NZ processed BSA). In some embodiments of any of the methods described herein, the culture medium containing processed BSA can contain between about 0.1 g/L to about 3.0 g/L (e.g., between about 0.1 g/L and about 2.9 g/L, between about 0.1 g/L and about 2.8 g/L, between about 0.1 g/L and about 2.7 g/L, between about 0.1 g/L and about 2.6 g/L, between about 0.1 g/L and about 2.5 g/L, between about 0.1 g/L and about 2.4 g/L, between about 0.1 g/L and about 2.3 g/L, between about 0.1 g/L and about 2.2 g/L, between about 0.1 g/L and about 2.1 g/L, between about 0.1 g/L and about 2.0 g/L, between about 0.1 g/L and about 1.9 g/L, between about 0.1 g/L and about 1.8 g/L, between about 0.1 g/L and about 1.7 g/L, between about 0.1 g/L and about 1.6 g/L, between about 0.1 g/L and about 1.5 g/L, between about 0.1 g/L and about 1.4 g/L, between about 0.1 g/L and about 1.3 g/L, between about 0.1 g/L and about 1.2 g/L, between about 0.1 g/L and about 1.1 g/L, between about 0.1 g/L and about 1.0 g/L, between about 0.1 g/L and about 0.9 g/L, between about 0.1 g/L and about 0.8 g/L, between about 0.1 g/L and about 0.7 g/L, between about 0.1 g/L and about 0.6 g/L, between about 0.1 g/L and about 0.5 g/L, between about 0.1 g/L and about 0.4 g/L, between about 0.1 g/L and about 0.3 g/L, between about 0.5 g/L and about 3.0 g/L, between about 0.5 g/L and about 2.9 g/L, between about 0.5 g/L and about 2.8 g/L, between about 0.5 g/L and about 2.7 g/L, between about 0.5 g/L and about 2.6 g/L, between about 0.5 g/L and about 2.5 g/L, between about 0.5 g/L and about 2.4 g/L, between about 0.5 g/L and about 2.3 g/L, between about 0.5 g/L and about 2.2 g/L, between about 0.5 g/L and about 2.1 g/L, between about 0.5 g/L and about 2.0 g/L, between about 0.5 g/L and about 1.9 g/L, between about 0.5 g/L and about 1.8 g/L, between about 0.5 g/L and about 1.7 g/L, between about 0.5 g/L and about 1.6 g/L, between about 0.5 g/L and about 1.5 g/L, between about 0.5 g/L and about 1.4 g/L, between about 0.5 g/L and about 1.3 g/L, between about 0.5 g/L and about 1.2 g/L, between about 0.5 g/L and about 1.1 g/L, between about 0.5 g/L and about 1.0 g/L, between about 0.5 g/L and about 0.9 g/L, between about 0.5 g/L and about 0.8 g/L, between about 0.5 g/L and about 0.7 g/L, between about 1.0 g/L and about 3.0 g/L, between about 1.0 g/L and about 2.9 g/L, between about 1.0 g/L and about 2.8 g/L, between about 1.0 g/L and about 2.7 g/L, between about 1.0 g/L and about 2.6 g/L, between about 1.0 g/L and about 2.5 g/L, between about 1.0 g/L and about 2.4 g/L, between about 1.0 g/L and about 2.3 g/L, between about 1.0 g/L and about 2.2 g/L, between about 1.0 g/L and about 2.1 g/L, between about 1.0 g/L and about 2.0 g/L, between about 1.0 g/L and about 1.9 g/L, between about 1.0 g/L and about 1.8 g/L, between about 1.0 g/L and about 1.7 g/L, between about 1.0 g/L and about 1.6 g/L, between about 1.0 g/L and about 1.5 g/L, between about 1.0 g/L and about 1.4 g/L, between about 1.0 g/L and about 1.3 g/L, between about 1.0 g/L and about 1.2 g/L, between about 1.5 g/L and about 3.0 g/L, between about 1.5 g/L and about 2.9 g/L, between about 1.5 g/L and about 2.8 g/L, between about 1.5 g/L and about 2.7 g/L, between about 1.5 g/L and about 2.6 g/L, between about 1.5 g/L and about 2.5 g/L, between about 1.5 g/L and about 2.4 g/L, between about 1.5 g/L and about 2.3 g/L, between about 1.5 g/L and about 2.2 g/L, between about 1.5 g/L and about 2.1 g/L, between about 1.5 g/L and about 2.0 g/L, between about 1.5 g/L and about 1.9 g/L, between about 1.5 g/L and about 1.8 g/L, between about 1.5 g/L and about 1.7 g/L, between about 2.0 g/L and about 3.0 g/L, between about 2.0 g/L and about 2.9 g/L, between about 2.0 g/L and about 2.8 g/L, between about 2.0 g/L and about 2.7 g/L, between about 2.0 g/L and about 2.6 g/L, between about 2.0 g/L and about 2.5 g/L, between about 2.0 g/L and about 2.4 g/L, between about 2.0 g/L and about 2.3 g/L, between about 2.0 g/L and about 2.2 g/L, between about 2.5 g/L and about 3.0 g/L, between about 2.5 g/L and about 2.9 g/L, between about 2.5 g/L and about 2.8 g/L, or between about 2.5 g/L and about 2.7 g/L) processed BSA.

The culture medium including 0.1 g/L or more processed BSA can the first culture medium, can be both the first culture medium and the feed culture medium, or can be or can be one or more of the first culture medium, the first feed culture medium, and the second feed culture medium. Fed batch culturing in any of the methods described herein can include the use of two different feed culture media, with one or both of the two different feed culture media including 0.1 g/L or more processed BSA.

As is well-known in the art, a culture medium containing processed BSA can be produced by adding a sufficient amount of processed BSA (in solid form or as a solution) to a liquid culture medium to achieve a desired final concentration of processed BSA in the liquid culture medium.

In some embodiments, the first culture medium contains a lipid solution (including oleic acid, linoleic acid, and cholesterol) at a concentration of about 1 mL of the lipid solution per 1 L of the first culture medium.

In some methods, the concentration of processed BSA present in the culture can remain substantially constant throughout the culturing period. In other methods, the concentration of processed BSA present in the culture can increase during the culturing period. In some embodiments, the processed BSA may be present in the liquid culture medium at the start of the culturing period (the first culture medium). In other embodiments, the processed BSA may be added to the first liquid culture medium after the start of the culturing period (e.g., by bolus injection or by adding a feed culture medium that contains a processed BSA).

Addition of Lipid Solution

The examples described herein can further include adding a bolus of a lipid solution (e.g., a lipid solution including oleic acid, linoleic acid, and cholesterol) to the culture when the cells reach a density of, e.g., about $1.0 \times 10^6$ cells/mL, about $1.1 \times 10^6$ cells/mL, about $1.2 \times 10^6$ cells/mL, about $1.3 \times 10^6$ cells/mL, about $1.4 \times 10^6$ cells/mL, about $1.5 \times 10^6$ cells/mL, about $1.6 \times 10^6$ cells/mL, about $1.7 \times 10^6$ cells/mL, about $1.8 \times 10^6$ cells/mL, about $1.9 \times 10^6$ cells/mL, about $2.0 \times 10^6$ cells/mL, about $2.1 \times 10^6$ cells/mL, about $2.2 \times 10^6$ cells/mL, about $2.3 \times 10^6$ cells/mL, about $2.4 \times 10^6$ cells/mL, about $2.5 \times 10^6$ cells/mL, between about $1.0 \times 10^6$ cells/mL and about $2.5 \times 10^6$ cells/mL, between about $1.0 \times 10^6$ cells/mL and about $2.4 \times 10^6$ cells/mL, between about $1.0 \times 10^6$ cells/mL and about $2.3 \times 10^6$ cells/mL, between about $1.0 \times 10^6$ cells/mL and about $2.2 \times 10^6$ cells/mL, between about $1.0 \times 10^6$ cells/mL and about $2.1 \times 10^6$ cells/mL, between about $1.0 \times 10^6$ cells/mL and about $2.0 \times 10^6$ cells/mL, between about $1.0 \times 10^6$ cells/mL and about $1.9 \times 10^6$ cells/mL, between about $1.0 \times 10^6$ cells/mL and about $1.8 \times 10^6$ cells/mL, between about $1.0 \times 10^6$ cells/mL and about $1.7 \times 10^6$ cells/mL, between about $1.0 \times 10^6$ cells/mL and about $1.6 \times 10^6$ cells/mL, between about $1.0 \times 10^6$ cells/mL and about $1.5 \times 10^6$ cells/mL, between about $1.0 \times 10^6$ cells/mL and about $1.4 \times 10^6$ cells/mL, between about $1.0 \times 10^6$ cells/mL and about $1.3 \times 10^6$ cells/mL, between about $1.0 \times 10^6$ cells/mL and about $1.2 \times 10^6$ cells/mL, between about $1.1 \times 10^6$ cells/mL and about $2.5 \times 10^6$ cells/mL, between about $1.1 \times 10^6$ cells/mL and about $2.4 \times 10^6$ cells/mL, between about $1.1 \times 10^6$ cells/mL and about $2.3 \times 10^6$ cells/mL, between about $1.1 \times 10^6$ cells/mL and about $2.2 \times 10^6$ cells/L, between about $1.1 \times 10^6$ cells/mL and about $2.1 \times 10^6$ cells/mL, between about $1.1 \times 10^6$ cells/mL and about $2.0 \times 10^6$ cells/mL, between about $1.1 \times 10^6$ cells/mL and about $1.9 \times 10^6$ cells/mL, between about $1.1 \times 10^6$ cells/mL and about $1.8 \times 10^6$ cells/mL, between about $1.1 \times 10^6$ cells/mL and about $1.7 \times 10^6$ cells/mL, between about $1.1 \times 10^6$ cells/mL and about $1.6 \times 10^6$ cells/mL, between about $1.1 \times 10^6$ cells/mL and about $1.5 \times 10^6$ cells/mL, between about $1.1 \times 10^6$ cells/mL and about $1.4 \times 10^6$ cells/mL, between about $1.1 \times 10^6$ cells/mL and about $1.3 \times 10^6$ cells/mL, between about $1.2 \times 10^6$ cells/mL and about $2.5 \times 10^6$ cells/mL, between about $1.2 \times 10^6$ cells/mL and about $2.4 \times 10^6$ cells/mL, between about $1.2 \times 10^6$ cells/mL and about $2.3 \times 10^6$ cells/mL, between about $1.2 \times 10^6$ cells/mL and about $2.2 \times 10^6$ cells/mL, between about $1.2 \times 10^6$ cells/mL and about $2.1 \times 10^6$ cells/mL, between about $1.2 \times 10^6$ cells/mL and about $2.0 \times 10^6$ cells/mL, between about $1.2 \times 10^6$ cells/mL and about $1.9 \times 10^6$ cells/mL, between about $1.2 \times 10^6$ cells/mL and about $1.8 \times 10^6$ cells/mL, between about $1.2 \times 10^6$ cells/mL and about $1.7 \times 10^6$ cells/mL, between about $1.2 \times 10^6$ cells/mL and about $1.6 \times 10^6$ cells/mL, between about $1.2 \times 10^6$ cells/mL and about $1.5 \times 10^6$ cells/mL, between about $1.2 \times 10^6$ cells/mL and about $1.4 \times 10^6$ cells/mL, between about $1.3 \times 10^6$ cells/mL and about $2.5 \times 10^6$ cells/mL, between about $1.3 \times 10^6$ cells/mL and about $2.4 \times 10^6$ cells/mL, between about $1.3 \times 10^6$ cells/mL and about $2.3 \times 10^6$ cells/mL, between about $1.3 \times 10^6$ cells/mL and about $2.2 \times 10^6$ cells/mL, between about $1.3 \times 10^6$ cells/mL and about $2.1 \times 10^6$ cells/mL, $1.3 \times 10^6$ cells/mL and about $2.0 \times 10^6$ cells/mL, between about $1.3 \times 10^6$ cells/mL and about $1.9 \times 10^6$ cells/mL, between about $1.3 \times 10^6$ cells/mL and about $1.8 \times 10^6$ cells/mL, between about $1.3 \times 10^6$ cells/mL and about $1.7 \times 10^6$ cells/mL, between about $1.3 \times 10^6$ cells/mL and about $1.6 \times 10^6$ cells/mL, $1.3 \times 10^6$ cells/mL and about $1.5 \times 10^6$ cells/mL, between about $1.4 \times 10^6$ cells/mL and about $2.5 \times 10^6$ cells/mL, between about $1.4 \times 10^6$ cells/mL and about $2.4 \times 10^6$ cells/mL, between about $1.4 \times 10^6$ cells/mL and about $2.3 \times 10^6$ cells/mL, between about $1.4 \times 10^6$ cells/mL and about $2.2 \times 10^6$ cells/mL, $1.4 \times 10^6$ cells/mL and about $2.1 \times 10^6$ cells/mL, between about $1.4 \times 10^6$ cells/mL and about $2.0 \times 10^6$ cells/mL, between about $1.4 \times 10^6$ cells/mL and about $1.9 \times 10^6$ cells/mL, between about $1.4 \times 10^6$ cells/mL and about $1.8 \times 10^6$ cells/mL, between about $1.4 \times 10^6$ cells/mL and about $1.7 \times 10^6$ cells/mL, between about $1.4 \times 10^6$ cells/mL and about $1.6 \times 10^6$ cells/mL, between about $1.5 \times 10^6$ cells/mL and about $2.5 \times 10^6$ cells/mL, between about $1.5 \times 10^6$ cells/mL and about $2.4 \times 10^6$ cells/mL, between about $1.5 \times 10^6$ cells/mL and about $2.3 \times 10^6$ cells/mL, between about $1.5 \times 10^6$ cells/mL and about $2.2 \times 10^6$ cells/mL, $1.5 \times 10^6$ cells/mL and about $2.1 \times 10^6$ cells/mL, between about $1.5 \times 10^6$ cells/mL and about $2.0 \times 10^6$ cells/mL, between about $1.5 \times 10^6$ cells/mL and about $1.9 \times 10^6$ cells/mL, between about $1.5 \times 10^6$ cells/mL and about $1.8 \times 10^6$ cells/mL, between about $1.5 \times 10^6$ cells/mL and about $1.7 \times 10^6$ cells/mL, between about $1.6 \times 10^6$ cells/mL and about $2.5 \times 10^6$ cells/mL, between about $1.6 \times 10^6$ cells/mL and about $2.4 \times 10^6$ cells/mL, between about $1.6 \times 10^6$ cells/mL and about $2.3 \times 10^6$ cells/mL, between about $1.6 \times 10^6$ cells/mL and about $2.2 \times 10^6$ cells/mL, $1.6 \times 10^6$ cells/mL and about $2.1 \times 10^6$ cells/mL, between about $1.6 \times 10^6$ cells/mL and about $2.0 \times 10^6$ cells/mL, between about $1.6 \times 10^6$ cells/mL and about $1.9 \times 10^6$ cells/mL, between about $1.6 \times 10^6$ cells/mL and about $1.8 \times 10^6$ cells/mL, between about $1.7 \times 10^6$ cells/mL and about $2.5 \times 10^6$ cells/mL, between about $1.7 \times 10^6$ cells/mL and about $2.4 \times 10^6$ cells/mL, between about $1.7 \times 10^6$ cells/mL and about $2.3 \times 10^6$ cells/mL, between about $1.7 \times 10^6$ cells/mL and about $2.2 \times 10^6$ cells/mL, $1.7 \times 10^6$ cells/mL and about $2.1 \times 10^6$ cells/mL, between about $1.7 \times 10^6$ cells/mL and about $2.0 \times 10^6$ cells/mL, between about $1.7 \times 10^6$ cells/mL and about $1.9 \times 10^6$ cells/mL, between about $1.8 \times 10^6$ cells/mL and about $2.5 \times 10^6$ cells/mL, between about $1.8 \times 10^6$ cells/mL and about $2.4 \times 10^6$ cells/mL, between about $1.8 \times 10^6$ cells/mL and about $2.3 \times 10^6$ cells/mL, between about $1.8 \times 10^6$ cells/mL and about $2.2 \times 10^6$ cells/mL, $1.8 \times 10^6$ cells/mL and about $2.1 \times 10^6$ cells/mL, between about $1.8 \times 10^6$ cells/mL and about $2.0 \times 10^6$ cells/mL, between about $1.9 \times 10^6$ cells/mL and about $2.5 \times 10^6$ cells/mL, between about $1.9 \times 10^6$ cells/mL and about $2.4 \times 10^6$ cells/mL, between about $1.9 \times 10^6$ cells/mL and about $2.3 \times 10^6$ cells/mL, between about $1.9 \times 10^6$ cells/mL and about $2.2 \times 10^6$ cells/mL, $1.9 \times 10^6$ cells/mL and about $2.1 \times 10^6$ cells/mL, between about $2.0 \times 10^6$ cells/mL and about $2.5 \times 10^6$ cells/mL, between about $2.0 \times 10^6$ cells/mL and about $2.4 \times 10^6$ cells/mL, between about $2.0 \times 10^6$ cells/mL and about $2.3 \times 10^6$ cells/mL, between about $2.0 \times 10^6$ cells/mL and about $2.2 \times 10^6$ cells/mL, between about $2.1 \times 10^6$ cells/mL and about $2.5 \times 10^6$ cells/mL, between about $2.1 \times 10^6$ cells/mL and about $2.4 \times 10^6$ cells/mL, between about $2.1 \times 10^6$ cells/mL and about $2.3 \times 10^6$ cells/mL, between about $2.2 \times 10^6$ cells/mL and about $2.5 \times 10^6$ cells/mL, between about $2.2 \times 10^6$ cells/mL and about $2.4 \times 10^6$ cells/mL, or between about $2.3 \times 10^6$ cells/mL and about $2.5 \times 10^6$ cells/mL.

In some embodiments 1 mL of lipid solution is added for, e.g., each about 0.85 L, each about 0.9 L, each about 0.95 L, each about 1.00 L, each about 1.05 L, each about 1.1 L, or each about 1.15 L of culture. For example, 4.2 mL of lipid solution is typically added to about 4.2 L of culture.

Addition of a Base Solution

The methods described herein further include adding a base solution (e.g., an alkali base solution) to the culture. A base solution can be, e.g., a buffered, sterile solution having a pH of about or greater than 8.0 (e.g., about or greater than 8.5, about or greater than 9.0, about or greater than 9.5, about or greater than 10.0, about or greater than 10.5, about or greater than 11.0, about or greater than 11.5, or about or greater than 12.0). A base solution can be, e.g., an alkali base solution. Non-limiting examples of alkali base solutions contain a concentration of (i) between about 0.5 M and about 1.0 M (e.g., between about 0.5 M and about 0.95 M, between about 0.5 M and about 0.9 M, between about 0.5 M and about 0.85 M, between about 0.5 M and about 0.8 M, between about 0.5 M and about 0.75 M, between about 0.5 M and about 0.70 M, between about 0.5 M and about 0.65 M, between about 0.5 M and about 0.6 M, between about 0.5 M and about 0.55 M, between about 0.55 M and about 1.0 M, between about 0.55 M and about 0.95 M, between about 0.55 M and about 0.9 M, between about 0.55 M and about 0.85 M, between about 0.55 M and about 0.8 M, between about 0.55 M and about 0.75 M, between about 0.55 M and about 0.7 M, between about 0.55 M and about 0.65 M, between about 0.55 M and about 0.6 M, between about 0.6 M and about 1.0 M, between about 0.6 M and about 0.95 M, between about 0.6 M and about 0.9 M, between about 0.6 M and about 0.85 M, between about 0.6 M and about 0.80 M, between about 0.6 M and about 0.75 M, between about 0.6 M and about 0.7 M, between about 0.6 M and about 0.65 M, between about 0.65 M and about 1.0 M, between about 0.65 M and about 0.95 M, between about 0.65 M and about 0.9 M, between about 0.65 M and about 0.85 M, between about 0.65 M and about 0.8 M, between about 0.65 M and about 0.75 M, between about 0.65 M and about 0.7 M, between about 0.7 M and about 1.0 M, between about 0.7 M and about 0.95 M, between about 0.7 M and about 0.9 M, between about 0.7 M and about 0.85 M, between about 0.7 M and about 0.8 M, between about 0.7 M and about 0.75 M, between about 0.75 M and about 1.0 M, between about 0.75 M and about 0.95 M, between about 0.75 M and about 0.9 M, between about 0.75 M and about 0.85 M, between about 0.75 M and about 0.8 M, between about 0.8 M and about 1.0 M, between about 0.8 M and about 0.95 M, between about 0.8 M and about 0.9 M, between about 0.8 M and about 0.85 M, between about 0.85 M and about 1.0 M, between about 0.85 M and about 0.95 M, between about 0.85 M and about 0.9 M, between about 0.9 M and about 1.0 M, between about 0.9 M and about 0.95 M, or between about 0.95 M and about 1.0 M) sodium carbonate and (ii) between about 0.25 M and about 0.75 M (e.g., between about 0.25 M and about 0.70 M, between about 0.25 M and about 0.65 M, between about 0.25 M and about 0.60 M, between about 0.25 M and about 0.55 M, between about 0.25 M and about 0.50 M, between about 0.25 M and about 0.45 M, between about 0.25 M and about 0.40 M, between about 0.25 M and about 0.35 M, between about 0.25 M and about 0.30 M, between about 0.30 M and about 0.75 M, between about 0.30 M and about 0.70 M, between about 0.30 M and about 0.65 M, between about 0.30 M and about 0.60 M, between about 0.30 M and about 0.55 M, between about 0.30 M and about 0.50 M, between about 0.30 M and about 0.45 M, between about 0.30 M and about 0.40 M, between about 0.30 and about 0.35 M, between about 0.35 M and about 0.75 M, between about 0.35 M and about 0.70 M, between about 0.35 M and about 0.65 M, between about 0.35 M and about 0.60 M, between about 0.35 M and about 0.55 M, between about 0.35 M and about 0.50 M, between about 0.35 M and about 0.45 M, between about 0.35 M and about 0.40 M, between about 0.4 M and about 0.75 M, between about 0.40 M and about 0.70 M, between about 0.40 M and about 0.65 M, between about 0.40 M and about 0.60 M, between about 0.40 M and about 0.55 M, between about 0.40 M and about 0.50 M, between about 0.40 M and about 0.45 M, between about 0.45 M and about 0.75 M, between about 0.45 M and about 0.70 M, between about 0.45 M and about 0.65 M, between about 0.45 M and about 0.60 M, between about 0.45 M and about 0.55 M, between about 0.45 M and about 0.50 M, between about 0.50 M and about 0.75 M, between about 0.50 M and about 0.70 M, between about 0.50 M and about 0.65 M, between about 0.50 M and about 0.60 M, between about 0.50 M and about 0.55 M, between about 0.55 M and about 0.75 M, between about 0.55 and about 0.70 M, between about 0.55 M and about 0.65 M, between about 0.55 M and about 0.60 M, between about 0.60 M and about 0.75 M, between about 0.60 M and about 0.70 M, between about 0.60 M and about 0.65 M, between about 0.65 M and about 0.75 M, between about 0.65 M and about 0.70 M, or between about 0.70 M and about 0.75 M) sodium bicarbonate. Additional examples of base solutions (e.g., alkali base solutions) that can be added to the culture are well-known in the art.

The base solution (e.g., alkali base solution) can be added to the culture continuously or periodically. The continuous addition of the alkali base solution to the culture can be started (initiated) at a time point that is about 5 hours to about 80 hours (e.g., about 5 hours to about 75 hours, about 5 hours to about 70 hours, about 5 hours to about 65 hours, about 5 hours to about 60 hours, about 5 hours to about 55 hours, about 5 hours to about 50 hours, about 5 hours to about 45 hours, about 5 hours to about 40 hours, about 5 hours to about 35 hours, about 5 hours to about 30 hours, about 5 hours to about 25 hours, about 5 hours to about 20 hours, about 5 hours to about 15 hours, about 10 hours to about 80 hours, about 10 hours to about 75 hours, about 10 hours to about 70 hours, about 10 hours to about 65 hours, about 10 hours to about 60 hours, about 10 hours to about 55 hours, about 10 hours to about 50 hours, about 10 hours to about 45 hours, about 10 hours to about 40 hours, about 10 hours to about 35 hours, about 10 hours to about 30 hours, about 10 hours to about 25 hours, about 10 hours to about 20 hours, about 10 hours to about 15 hours, about 15 hours to about 80 hours, about 15 hours to about 75 hours, about 15 hours to about 70 hours, about 15 hours to about 65 hours, about 15 hours to about 60 hours, about 15 hours to about 55 hours, about 15 hours to about 50 hours, about 15 hours to about 45 hours, about 15 hours to about 40 hours, about 15 hours to about 35 hours, about 15 hours to about 30 hours, about 15 hours to about 25 hours, about 20 hours to about 80 hours, about 20 hours to about 75 hours, about 20 hours to about 70 hours, about 20 hours to about 65 hours, about 20 hours to about 60 hours, about 20 hours to about 55 hours, about 20 hours to about 50 hours, about 20 hours to about 45 hours, about 20 hours to about 40 hours, about 20 hours to about 35 hours, about 20 hours to about 30 hours, about 20 hours to about 25 hours, about 25 hours to about 80 hours, about 25 hours to about 75 hours, about 25 hours to about 70 hours, about 25 hours to about 65 hours, about 25 hours to about 60 hours, about 25 hours to about 55 hours, about 25 hours to about 50 hours, about 25 hours to about 45 hours, about 25 hours to about 40 hours, about 25 hours to about 35 hours, about 30 hours to about 80 hours, about 30 hours to about 75 hours, about 30 hours to about 70 hour, about 30 hours to about 65 hours, about 30 hours to about 60 hours, about 30 hours to about 55 hours, about 30 hours to about 50 hours, about 30 hours to about 45 hours, about 30 hours to about 40 hours, about 35 hours to about 80 hours, about 35 hours to about 75 hours, about 35 hours to about 70 hours, about 35 hours to about 65 hours, about 35 hours to about 60 hours, about 35 hours to about 55 hours, about 35 hours to about 50 hours, about 35 hours to about 45 hours, about 40 hours to about 80 hours, about 40 hours to about 75 hours, about 40 hours to about 70 hours, about 40 hours to about 65 hours, about 40 hours to about 60 hours, about 40 hours to about 55 hours, about 40 hours to about 50 hours, about 45 hours to about 80 hours, about 45 hours to about 75 hours, about 45 hours to about 70 hours, about 45 hours to about 65 hours, about 45 hours to about 60 hours, about 45 hours to about 55 hours, about 50 hours to about 80 hours, about 50 hours to about 75 hours, about 50 hours to about 70 hours, about 50 hours to about 65 hours, about 50 hours to about 60 hours, about 55 hours to about 80 hours, about 55 hours to about 75 hours, about 55 hours to about 70 hours, about 55 hours to about 65 hours, about 60 hours to about 80 hours, about 60 hours to about 75 hours, about 60 hours to about 70 hours, about 65 hours to about 80 hours, about 65 hours to about 75 hours, or about 70 hours to about 80 hours) after the initial time point that the feed culture medium is added to the culture (e.g., any of the exemplary time points for initiating the addition of the feed culture medium to the culture described herein). In some embodiments, the addition of the base solution (e.g., alkali base solution) is initiated at a time point that is between about 70 hours to about 170 hours (e.g., between about 70 hours to about 165 hours, between about 70 hours to about 160 hours, between about 70 hours to about 155 hours, between about 70 hours and about 150 hours, between about 70 hours to about 145 hours, between about 70 hours to about 140 hours, between about 70 hours to about 135 hours, between about 70 hours to about 130 hours, between about 70 hours to about 125 hours, between about 70 hours to about 120 hours, between about 70 hours to about 115 hours, between about 70 hours to about 110 hours, between about 70 hours to about 105 hours, between about 70 hours to about 100 hours, between about 70 hours to about 95 hours, between about 70 hours to about 90 hours, between about 70 hours to about 85 hours, between about 70 hours to about 80 hours, between about 75 hours to about 170 hours, between about 75 hours to about 165 hours, between about 75 hours to about 160 hours, between about 75 hours to about 155 hours, between about 75 hours and about 150 hours, between about 75 hours to about 145 hours, between about 75 hours to about 140 hours, between about 75 hours to about 135 hours, between about 75 hours to about 130 hours, between about 75 hours to about 125 hours, between about 75 hours to about 120 hours, between about 75 hours to about 115 hours, between about 75 hours to about 110 hours, between about 75 hours to about 105 hours, between about 75 hours to about 100 hours, between about 75 hours to about 95 hours, between about 75 hours to about 90 hours, between about 75 hours to about 85 hours, between about 80 hours to about 170 hours, between about 80 hours to about 165 hours, between about 80 hours to about 160 hours, between about 80 hours to about 155 hours, between about 80 hours and about 150 hours, between about 80 hours to about 145 hours, between about 80 hours to about 140 hours, between about 80 hours to about 135 hours, between about 80 hours to about 130 hours, between about 80 hours to about 125 hours, between about 80 hours to about 120 hours, between about 80 hours to about 115 hours, between about 80 hours to about 110 hours, between about 80 hours to about 105 hours, between about 80 hours to about 100 hours, between about 80 hours to about 95 hours, between about 80 hours to about 90 hours, between about 85 hours to about 170 hours, between about 85 hours to about 165 hours, between about 85 hours to about 160 hours, between about 85 hours to about 155 hours, between about 85 hours and about 150 hours, between about 85 hours to about 145 hours, between about 85 hours to about 140 hours, between about 85 hours to about 135 hours, between about 85 hours to about 130 hours, between about 85 hours to about 125 hours, between about 85 hours to about 120 hours, between about 85 hours to about 115 hours, between about 85 hours to about 110 hours, between about 85 hours to about 105 hours, between about 85 hours to about 100 hours, between about 85 hours to about 95 hours, between about 90 hours to about 170 hours, between about 90 hours to about 165 hours, between about 90 hours to about 160 hours, between about 90 hours to about 155 hours, between about 90 hours and about 150 hours, between about 90 hours to about 145 hours, between about 90 hours to about 140 hours, between about 90 hours to about 135 hours, between about 90 hours to about 130 hours, between about 90 hours to about 125 hours, between about 90 hours to about 120 hours, between about 90 hours to about 115 hours, between about 90 hours to about 110 hours, between about 90 hours to about 105 hours, between about 90 hours to about 100 hours, between about 95 hours to about 170 hours, between about 95 hours to about 165 hours, between about 95 hours to about 160 hours, between about 95 hours to about 155 hours, between about 95 hours and about 150 hours, between about 95 hours to about 145 hours, between about 95 hours to about 140 hours, between about 95 hours to about 135 hours, between about 95 hours to about 130 hours, between about 95 hours to about 125 hours, between about 95 hours to about 120 hours, between about 95 hours to about 115 hours, between about 95 hours to about 110 hours, between about 95 hours to about 105 hours, between about 100 hours to about 170 hours, between about 100 hours to about 165 hours, between about 100 hours to about 160 hours, between about 100 hours to about 155 hours, between about 100 hours and about 150 hours, between about 100 hours to about 145 hours, between about 100 hours to about 140 hours, between about 100 hours to about 135 hours, between about 100 hours to about 130 hours, between about 100 hours to about 125 hours, between about 100 hours to about 120 hours, between about 100 hours to about 115 hours, between about 100 hours to about 110 hours, between about 105 hours to about 170 hours, between about 105 hours to about 165 hours, between about 105 hours to about 160 hours, between about 105 hours to about 155 hours, between about 105 hours and about 150 hours, between about 105 hours to about 145 hours, between about 105 hours to about 140 hours, between about 105 hours to about 135 hours, between about 105 hours to about 130 hours, between about 105 hours to about 125 hours, between about 105 hours to about 120 hours, between about 105 hours to about 115 hours, between about 110 hours to about 170 hours, between about 110 hours to about 165 hours, between about 110 hours to about 160 hours, between about 110 hours to about 155 hours, between about 110 hours and about 150 hours, between about 110 hours to about 145 hours, between about 110 hours to about 140 hours, between about 110 hours to about 135 hours, between about 110 hours to about 130 hours, between about 110 hours to about 125 hours, between about 110 hours to about 120 hours, between about 115 hours to about 170 hours, between about 115 hours to about 165 hours, between about 115 hours to about 160 hours, between about 115 hours to about 155 hours, between about 115 hours and about 150 hours, between about 115 hours to about 145 hours, between about 115 hours to about 140 hours, between about 115 hours to about 135 hours, between about 115 hours to about 130 hours, between about 115 hours to about 125 hours, between about 120 hours to about 170 hours, between about 120 hours to about 165 hours, between about 120 hours to about 160 hours, between about 120 hours to about 155 hours, between about 120 hours and about 150 hours, between about 120 hours to about 145 hours, between about 120 hours to about 140 hours, between about 120 hours to about 135 hours, between about 120 hours to about 130 hours, between about 125 hours to about 170 hours, between about 125 hours to about 165 hours, between about 125 hours to about 160 hours, between about 125 hours to about 155 hours, between about 125 hours and about 150 hours, between about 125 hours to about 145 hours, between about 125 hours to about 140 hours, between about 125 hours to about 135 hours, between about 130 hours to about 170 hours, between about 130 hours to about 165 hours, between about 130 hours to about 160 hours, between about 130 hours to about 155 hours, between about 130 hours and about 150 hours, between about 130 hours to about 145 hours, between about 130 hours to about 140 hours, between about 135 hours to about 170 hours, between about 135 hours to about 165 hours, between about 135 hours to about 160 hours, between about 135 hours to about 155 hours, between about 135 hours and about 150 hours, between about 135 hours to about 145 hours, between about 140 hours to about 170 hours, between about 140 hours to about 165 hours, between about 140 hours to about 160 hours, between about 140 hours to about 155 hours, between about 140 hours and about 150 hours, between about 145 hours to about 170 hours, between about 145 hours to about 165 hours, between about 145 hours to about 160 hours, between about 145 hours to about 155 hours, between about 150 hours to about 170 hours, between about 150 hours to about 165 hours, between about 150 hours to about 160 hours, between about 155 hours to about 170 hours, between about 155 hours to about 165 hours, or between about 160 hours to about 170 hours) after the start of the culturing period.

The rate of addition of base solution (e.g., alkali base solution) to the culture can be, e.g., between about 10 µL/minute to about 120 µL/minute, between about 10 µL/minute to about 115 µL/minute, between about 10 µL/minute to about 110 µL/minute, between about 10 µL/minute to about 105 µL/minute, between about 10 µL/minute to about 100 µL/minute, between about 10 µL/minute to about 95 µL/minute, between about 10 µL/minute to about 90 µL/minute, between about 10 µL/minute to about 85 µL/minute, between about 10 µL/minute to about 80 µL/minute, 10 µL/minute to about 75 µL/minute, between about 10 µL/minute to about 70 µL/minute, between about 10 µL/minute to about 65 µL/minute, between about 10 µL/minute to about 60 µL/minute, between about 10 µL/minute to about 55 µL/minute, between about 10 µL/minute to about 50 µL/minute, between about 10 µL/minute to about 45 µL/minute, between about 10 µL/minute to about 40 µL/minute, between about 10 µL/minute to about 35 µL/minute, between about 10 µL/minute to about 30 µL/minute, between about 10 µL/minute to about 25 µL/minute, between about 10 µL/minute to about 20 µL/minute, between about 15 µL/minute to about 120 µL/minute, between about 15 µL/minute to about 115 µL/minute, between about 15 µL/minute to about 110 µL/minute, between about 15 µL/minute to about 105 µL/minute, between about 15 µL/minute to about 100 µL/minute, between about 15 µL/minute to about 95 µL/minute, between about 15 µL/minute to about 90 µL/minute, between about 15 µL/minute to about 85 µL/minute, between about 15 µL/minute to about 80 µL/minute, 15 µL/minute to about 75 µL/minute, between about 15 µL/minute to about 70 µL/minute, between about 15 µL/minute to about 65 µL/minute, between about 15 µL/minute to about 60 µL/minute, between about 15 µL/minute to about 55 µL/minute, between about 15 µL/minute to about 50 µL/minute, between about 15 µL/minute to about 45 µL/minute, between about 15 µL/minute to about 40 µL/minute, between about 15 µL/minute to about 35 µL/minute, between about 15 µL/minute to about 30 µL/minute, between about 15 µL/minute to about 25 µL/minute, between about 20 µL/minute to about 120 µL/minute, between about 20 µL/minute to about 115 µL/minute, between about 20 µL/minute to about 110 µL/minute, between about 20 µL/minute to about 105 µL/minute, between about 20 µL/minute to about 100 µL/minute, between about 20 µL/minute to about 95 µL/minute, between about 20 µL/minute to about 90 µL/minute, between about 20 µL/minute to about 85 µL/minute, between about 20 µL/minute to about 80 µL/minute, 20 µL/minute to about 75 µL/minute, between about 20 µL/minute to about 70 µL/minute, between about 20 µL/minute to about 65 µL/minute, between about 20 µL/minute to about 60 µL/minute, between about 20 µL/minute to about 55 µL/minute, between about 20 µL/minute to about 50 µL/minute, between about 20 µL/minute to about 45 µL/minute, between about 20 µL/minute to about 40 µL/minute, between about 20 µL/minute to about 35 µL/minute, between about 20 µL/minute to about 30 µL/minute, between about 25 µL/minute to about 120 µL/minute, between about 25 µL/minute to about 115 µL/minute, between about 25 µL/minute to about 110 µL/minute, between about 25 µL/minute to about 105 µL/minute, between about 25 µL/minute to about 100 µL/minute, between about 25 µL/minute to about 95 µL/minute, between about 25 µL/minute to about 90 µL/minute, between about 25 µL/minute to about 85 µL/minute, between about 25 µL/minute to about 80 µL/minute, 25 µL/minute to about 75 µL/minute, between about 25 µL/minute to about 70 µL/minute, between about 25 µL/minute to about 65 µL/minute, between about 25 µL/minute to about 60 µL/minute, between about 25 µL/minute to about 55 µL/minute, between about 25 µL/minute to about 50 µL/minute, between about 25 µL/minute to about 45 µL/minute, between about 25 µL/minute to about 40 µL/minute, between about 25 µL/minute to about 35 µL/minute, between about 30 µL/minute to about 120 µL/minute, between about 30 µL/minute to about 115 µL/minute, between about 30 µL/minute to about 110 µL/minute, between about 30 µL/minute to about 105 µL/minute, between about 30 µL/minute to about 100 µL/minute, between about 30 µL/minute to about 95 µL/minute, between about 30 µL/minute to about 90 µL/minute, between about 30 µL/minute to about 85 µL/minute, between about 30 µL/minute to about 80 µL/minute, 30 µL/minute to about 75 µL/minute, between about 30 µL/minute to about 70 µL/minute, between about 30 µL/minute to about 65 µL/minute, between about 30 µL/minute to about 60 µL/minute, between about 30 µL/minute to about 55 µL/minute, between about 30 µL/minute to about 50 µL/minute, between about 30 µL/minute to about 45

μL/minute, between about 30 μL/minute to about 40 μL/minute, between about 35 μL/minute to about 120 μL/minute, between about 35 μL/minute to about 115 μL/minute, between about 35 μL/minute to about 110 μL/minute, between about 35 μL/minute to about 105 μL/minute, between about 35 μL/minute to about 100 μL/minute, between about 35 μL/minute to about 95 μL/minute, between about 35 μL/minute to about 90 μL/minute, between about 35 μL/minute to about 85 μL/minute, between about 35 μL/minute to about 80 μL/minute, 35 μL/minute to about 75 μL/minute, between about 35 μL/minute to about 70 μL/minute, between about 35 μL/minute to about 65 μL/minute, between about 35 μL/minute to about 60 μL/minute, between about 35 μL/minute to about 55 μL/minute, between about 35 μL/minute to about 50 μL/minute, between about 35 μL/minute to about 45 μL/minute, between about 40 μL/minute to about 120 μL/minute, between about 40 μL/minute to about 115 μL/minute, between about 40 μL/minute to about 110 μL/minute, between about 40 μL/minute to about 105 μL/minute, between about 40 μL/minute to about 100 μL/minute, between about 40 μL/minute to about 95 μL/minute, between about 40 μL/minute to about 90 μL/minute, between about 40 μL/minute to about 85 μL/minute, between about 40 μL/minute to about 80 μL/minute, 40 μL/minute to about 75 μL/minute, between about 40 μL/minute to about 70 μL/minute, between about 40 μL/minute to about 65 μL/minute, between about 40 μL/minute to about 60 μL/minute, between about 40 μL/minute to about 55 μL/minute, between about 40 μL/minute to about 50 μL/minute, between about 45 μL/minute to about 120 μL/minute, between about 45 μL/minute to about 115 μL/minute, between about 45 μL/minute to about 110 μL/minute, between about 45 μL/minute to about 105 μL/minute, between about 45 μL/minute to about 100 μL/minute, between about 45 μL/minute to about 95 μL/minute, between about 45 μL/minute to about 90 μL/minute, between about 45 μL/minute to about 85 μL/minute, between about 45 μL/minute to about 80 μL/minute, 45 μL/minute to about 75 μL/minute, between about 45 μL/minute to about 70 μL/minute, between about 45 μL/minute to about 65 μL/minute, between about 45 μL/minute to about 60 μL/minute, between about 45 μL/minute to about 55 μL/minute, between about 50 μL/minute to about 120 μL/minute, between about 50 μL/minute to about 115 μL/minute, between about 50 μL/minute to about 110 μL/minute, between about 50 μL/minute to about 105 μL/minute, between about 50 μL/minute to about 100 μL/minute, between about 50 μL/minute to about 95 μL/minute, between about 50 μL/minute to about 90 μL/minute, between about 50 μL/minute to about 85 μL/minute, between about 50 μL/minute to about 80 μL/minute, 50 μL/minute to about 75 μL/minute, between about 50 μL/minute to about 70 μL/minute, between about 50 μL/minute to about 65 μL/minute, between about 50 μL/minute to about 60 μL/minute, between about 55 μL/minute to about 120 μL/minute, between about 55 μL/minute to about 115 μL/minute, between about 55 μL/minute to about 110 μL/minute, between about 55 μL/minute to about 105 μL/minute, between about 55 μL/minute to about 100 μL/minute, between about 55 μL/minute to about 95 μL/minute, between about 55 μL/minute to about 90 μL/minute, between about 55 μL/minute to about 85 μL/minute, between about 55 μL/minute to about 80 μL/minute, 55 μL/minute to about 75 μL/minute, between about 55 μL/minute to about 70 μL/minute, between about 55 μL/minute to about 65 μL/minute, between about 60 μL/minute to about 120 μL/minute, between about 60 μL/minute to about 115 μL/minute, between about 60 μL/minute to about 110 μL/minute, between about 60 μL/minute to about 105 μL/minute, between about 60 μL/minute to about 100 μL/minute, between about 60 μL/minute to about 95 μL/minute, between about 60 μL/minute to about 90 μL/minute, between about 60 μL/minute to about 85 μL/minute, between about 60 μL/minute to about 80 μL/minute, 60 μL/minute to about 75 μL/minute, between about 60 μL/minute to about 70 μL/minute, between about 65 μL/minute to about 120 μL/minute, between about 65 μL/minute to about 115 μL/minute, between about 65 μL/minute to about 110 μL/minute, between about 65 μL/minute to about 105 μL/minute, between about 65 μL/minute to about 100 μL/minute, between about 65 μL/minute to about 95 μL/minute, between about 65 μL/minute to about 90 μL/minute, between about 65 μL/minute to about 85 μL/minute, between about 65 μL/minute to about 80 μL/minute, 65 μL/minute to about 75 μL/minute, between about 70 μL/minute to about 120 μL/minute, between about 70 μL/minute to about 115 μL/minute, between about 70 μL/minute to about 110 μL/minute, between about 70 μL/minute to about 105 μL/minute, between about 70 μL/minute to about 100 μL/minute, between about 70 μL/minute to about 95 μL/minute, between about 70 μL/minute to about 90 μL/minute, between about 70 μL/minute to about 85 μL/minute, between about 70 μL/minute to about 80 μL/minute, between about 75 μL/minute to about 120 μL/minute, between about 75 μL/minute to about 115 μL/minute, between about 75 μL/minute to about 110 μL/minute, between about 75 μL/minute to about 105 μL/minute, between about 75 μL/minute to about 100 μL/minute, between about 75 μL/minute to about 95 μL/minute, between about 75 μL/minute to about 90 μL/minute, between about 75 μL/minute to about 85 μL/minute, between about 80 μL/minute to about 120 μL/minute, between about 80 μL/minute to about 115 μL/minute, between about 80 μL/minute to about 110 μL/minute, between about 80 μL/minute to about 105 μL/minute, between about 80 μL/minute to about 100 μL/minute, between about 80 μL/minute to about 95 μL/minute, between about 80 μL/minute to about 90 μL/minute, between about 85 μL/minute to about 120 μL/minute, between about 85 μL/minute to about 115 μL/minute, between about 85 μL/minute to about 110 μL/minute, between about 85 μL/minute to about 105 μL/minute, between about 85 μL/minute to about 100 μL/minute, between about 85 μL/minute to about 95 μL/minute, between about 90 μL/minute to about 120 μL/minute, between about 90 μL/minute to about 115 μL/minute, between about 90 μL/minute to about 110 μL/minute, between about 90 μL/minute to about 105 μL/minute to about 100 μL/minute, about 95 μL/minute to about 120 μL/minute, between about 95 μL/minute to about 115 μL/minute, between about 95 μL/minute to about 110 μL/minute, between about 95 μL/minute to about 105 μL/minute, about 100 μL/minute to about 120 μL/minute, between about 100 μL/minute to about 115 μL/minute, between about 100 μL/minute to about 110 μL/minute, about 105 μL/minute to about 120 μL/minute, between about 105 μL/minute to about 115 μL/minute, or about 110 μL/minute to about 120 μL/minute.

The rate of addition of base solution (e.g., alkali base solution) to the culture can be, e.g., between about 0.3 mL/hour to about 7 mL/hour, between about 0.3 mL/hour to about 6 mL/hour, between about 0.3 mL/hour to about 5 mL/hour, between about 0.3 mL/hour to about 4 mL/hour, between about 0.3 mL/hour to about 3 mL/hour, between about 0.3 mL/hour to about 2 mL/hour, between about 0.3 mL/hour to about 1.95 mL/hour, between about 0.3 mL/hour to about 1.90 mL/hour, between about 0.3 mL/hour to about 1.85 mL/hour, between about 0.3 mL/hour to about 1.80 mL/hour, between about 0.3 mL/hour to about 1.75 mL/hour, between about 0.3 mL/hour to about 1.70 mL/hour, between about 0.3 mL/hour to about 1.65 mL/hour, between about 0.3 mL/hour to about 1.60 mL/hour, between about 0.3 mL/hour to about 1.55 mL/hour, between about 0.3 mL/hour to about 1.50 mL/hour, between about 0.3 mL/hour to about 1.45 mL/hour, between about 0.3 mL/hour to about 1.40 mL/hour, between about 0.3 mL/hour to about 1.35 mL/hour, between about 0.3 mL/hour to about 1.30 mL/hour, between about 0.3 mL/hour to about 1.25 mL/hour, between about 0.3 mL/hour to about 1.20 mL/hour, between about 0.3 mL/hour to about 1.15 mL/hour, between about 0.3 mL/hour to about 1.10 mL/hour, between about 0.3 mL/hour to about 1.05 mL/hour, between about 0.3 mL/hour to about 1.00 mL/hour, between about 0.3 mL/hour to about 0.8 mL/hour, between about 0.3 mL/hour to about 0.6 mL/hour, between about 0.5 mL/hour to about 7 mL/hour, between about 0.5 mL/hour to about 6 mL/hour, between about 0.5 mL/hour to about 5 mL/hour, between about 0.5 mL/hour to about 4 mL/hour, between about 0.5 mL/hour to about 3 mL/hour, between about 0.5 mL/hour to about 2 mL/hour, between about 0.5 mL/hour to about 1.95 mL/hour, between about 0.5 mL/hour to about 1.90 mL/hour, between about 0.5 mL/hour to about 1.85 mL/hour, between about 0.5 mL/hour to about 1.80 mL/hour, between about 0.5 mL/hour to about 1.75 mL/hour, between about 0.5 mL/hour to about 1.70 mL/hour, between about 0.5 mL/hour to about 1.65 mL/hour, between about 0.5 mL/hour to about 1.60 mL/hour, between about 0.5 mL/hour to about 1.55 mL/hour, between about 0.5 mL/hour to about 1.50 mL/hour, between about 0.5 mL/hour to about 1.45 mL/hour, between about 0.5 mL/hour to about 1.40 mL/hour, between about 0.5 mL/hour to about 1.35 mL/hour, between about 0.5 mL/hour to about 1.30 mL/hour, between about 0.5 mL/hour to about 1.25 mL/hour, between about 0.5 mL/hour to about 1.20 mL/hour, between about 0.5 mL/hour to about 1.15 mL/hour, between about 0.5 mL/hour to about 1.10 mL/hour, between about 0.5 mL/hour to about 1.05 mL/hour, between about 0.5 mL/hour to about 1.00 mL/hour, between about 0.5 mL/hour to about 0.8 mL/hour, between about 1.0 mL/hour to about 7 mL/hour, between about 1.0 mL/hour to about 6 mL/hour, between about 1.0 mL/hour to about 5 mL/hour, between about 1.0 mL/hour to about 4 mL/hour, between about 1.0 mL/hour to about 3 mL/hour, between about 1.0 mL/hour to about 2 mL/hour, between about 1.0 mL/hour to about 1.95 mL/hour, between about 1.0 mL/hour to about 1.90 mL/hour, between about 1.0 mL/hour to about 1.85 mL/hour, between about 1.0 mL/hour to about 1.80 mL/hour, between about 1.0 mL/hour to about 1.75 mL/hour, between about 1.0 mL/hour to about 1.70 mL/hour, between about 1.0 mL/hour to about 1.65 mL/hour, between about 1.0 mL/hour to about 1.60 mL/hour, between about 1.0 mL/hour to about 1.55 mL/hour, between about 1.0 mL/hour to about 1.50 mL/hour, between about 1.0 mL/hour to about 1.45 mL/hour, between about 1.0 mL/hour to about 1.40 mL/hour, between about 1.0 mL/hour to about 1.35 mL/hour, between about 1.0 mL/hour to about 1.30 mL/hour, between about 1.0 mL/hour to about 1.25 mL/hour, between about 1.0 mL/hour to about 1.20 mL/hour, between about 1.0 mL/hour to about 1.15 mL/hour, between about 1.0 mL/hour to about 1.10 mL/hour, between about 1.2 mL/hour to about 7 mL/hour, between about 1.2 mL/hour to about 6 mL/hour, between about 1.2 mL/hour to about 5 mL/hour, between about 1.2 mL/hour to about 4 mL/hour, between about 1.2 mL/hour to about 3 mL/hour, between about 1.2 mL/hour to about 2 mL/hour, between about 1.2 mL/hour to about 1.95 mL/hour, between about 1.2 mL/hour to about 1.90 mL/hour, between about 1.2 mL/hour to about 1.85 mL/hour, between about 1.2 mL/hour to about 1.80 mL/hour, between about 1.2 mL/hour to about 1.75 mL/hour, between about 1.2 mL/hour to about 1.70 mL/hour, between about 1.2 mL/hour to about 1.65 mL/hour, between about 1.2 mL/hour to about 1.60 mL/hour, between about 1.2 mL/hour to about 1.55 mL/hour, between about 1.2 mL/hour to about 1.50 mL/hour, between about 1.2 mL/hour to about 1.45 mL/hour, between about 1.2 mL/hour to about 1.40 mL/hour, between about 1.2 mL/hour to about 1.35 mL/hour, between about 1.2 mL/hour to about 1.30 mL/hour, between about 1.4 mL/hour to about 7 mL/hour, between about 1.4 mL/hour to about 6 mL/hour, between about 1.4 mL/hour to about 5 mL/hour, between about 1.4 mL/hour to about 4 mL/hour, between about 1.4 mL/hour to about 3 mL/hour, between about 1.4 mL/hour to about 2 mL/hour, between about 1.4 mL/hour to about 1.95 mL/hour, between about 1.4 mL/hour to about 1.90 mL/hour, between about 1.4 mL/hour to about 1.85 mL/hour, between about 1.4 mL/hour to about 1.80 mL/hour, between about 1.4 mL/hour to about 1.75 mL/hour, between about 1.4 mL/hour to about 1.70 mL/hour, between about 1.4 mL/hour to about 1.65 mL/hour, between about 1.4 mL/hour to about 1.60 mL/hour, between about 1.4 mL/hour to about 1.55 mL/hour, between about 1.4 mL/hour to about 1.50 mL/hour, between about 1.6 mL/hour to about 7 mL/hour, between about 1.6 mL/hour to about 6 mL/hour, between about 1.6 mL/hour to about 5 mL/hour, between about 1.6 mL/hour to about 4 mL/hour, between about 1.6 mL/hour to about 3 mL/hour, between about 1.6 mL/hour to about 2 mL/hour, between about 1.6 mL/hour to about 1.95 mL/hour, between about 1.6 mL/hour to about 1.90 mL/hour, between about 1.6 mL/hour to about 1.85 mL/hour, between about 1.6 mL/hour to about 1.80 mL/hour, between about 1.6 mL/hour to about 1.75 mL/hour, between about 1.6 mL/hour to about 1.70 mL/hour, between about 1.65 mL/hour to about 7 mL/hour, between about 1.65 mL/hour to about 6 mL/hour, between about 1.65 mL/hour to about 5 mL/hour, between about 1.65 mL/hour to about 4 mL/hour, between about 1.65 mL/hour to about 3 mL/hour, between about 1.65 mL/hour to about 2 mL/hour, between about 1.65 mL/hour to about 1.95 mL/hour, between about 1.65 mL/hour to about 1.90 mL/hour, between about 1.65 mL/hour to about 1.85 mL/hour, between about 1.65 mL/hour to about 1.80 mL/hour, between about 1.65 mL/hour to about 1.75 mL/hour, between about 1.70 mL/hour to about 7 mL/hour, between about 1.70 mL/hour to about 6 mL/hour, between about 1.70 mL/hour to about 5 mL/hour, between about 1.70 mL/hour to about 4 mL/hour, between about 1.70 mL/hour to about 3 mL/hour, between about 1.70 mL/hour to about 2 mL/hour, between about 1.70 mL/hour to about 1.95 mL/hour, between about 1.70 mL/hour to about 1.90 mL/hour, between about 1.70 mL/hour to about 1.85 mL/hour, between about 1.70 mL/hour to about 1.80 mL/hour, between about 1.75 mL/hour to about 7 mL/hour, between about 1.75 mL/hour to about 6 mL/hour, between about 1.75 mL/hour to about 5 mL/hour, between about 1.75 mL/hour to about 4 mL/hour, between about 1.75 mL/hour to about 3 mL/hour, between about 1.75 mL/hour to about 2 mL/hour, between about 1.75 mL/hour to about 1.95 mL/hour, between about 1.75 mL/hour to about 1.90 mL/hour, between about 1.75 mL/hour to about 1.85 mL/hour, between about 1.80 mL/hour to about 7 mL/hour, between about 1.80 mL/hour to about 6 mL/hour, between about 1.80 mL/hour to about 5 mL/hour, between about 1.80 mL/hour to about 4 mL/hour, between about 1.80 mL/hour to about 3 mL/hour, between about 1.80 mL/hour to about 2 mL/hour, between about 1.80 mL/hour to about 1.95 mL/hour, between about 1.80 mL/hour to about 1.90 mL/hour, between about 1.85 mL/hour to about 7 mL/hour, between about 1.85 mL/hour to about 6 mL/hour, between about 1.85 mL/hour to about 5 mL/hour, between about 1.85 mL/hour to about 4 mL/hour, between about 1.85 mL/hour to about 3 mL/hour, between about 1.85 mL/hour to about 2 mL/hour, between about 1.85 mL/hour to about 1.95 mL/hour, between about 1.90 mL/hour to about 7 mL/hour, between about 1.90 mL/hour to about 6 mL/hour, between about 1.90 mL/hour to about 5 mL/hour, between about 1.90 mL/hour to about 4 mL/hour, between about 1.90 mL/hour to about 3 mL/hour, between about 1.90 mL/hour to about 2 mL/hour, between about 1.95 mL/hour to about 7 mL/hour, between about 1.95 mL/hour to about 6 mL/hour, between about 1.95 mL/hour to about 5 mL/hour, between about 1.95 mL/hour to about 4 mL/hour, between about 1.95 mL/hour to about 3 mL/hour, between about 1.95 mL/hour to about 2 mL/hour, between about 2.0 mL/hour to about 7 mL/hour, between about 2.0 mL/hour to about 6 mL/hour, between about 2.0 mL/hour to about 5 mL/hour, between about 2.0 mL/hour to about 4 mL/hour, between about 2.0 mL/hour to about 3 mL/hour, between about 3.0 mL/hour to about 7 mL/hour, between about 3.0 mL/hour to about 6 mL/hour, between about 3.0 mL/hour to about 5 mL/hour, between about 3.0 mL/hour to about 4 mL/hour, between about 4.0 mL/hour to about 7 mL/hour, between about 4.0 mL/hour to about 6 mL/hour, between about 4.0 mL/hour to about 5 mL/hour, between about 5.0 mL/hour to about 7 mL/hour, between about 5.0 mL/hour to about 6 mL/hour, or between about 6.0 mL/hour to about 7 mL/hour.

The total volume of the base solution (e.g., alkali base solution) to the culture over the entire culturing period can be between about 50 mL and about 1100 mL (e.g., between about 50 mL and about 1000 mL, between about 50 mL and about 800 mL, between about 50 mL and about 600 mL, between about 50 mL and about 400 mL, between about 50 mL and about 200 mL, between about 50 mL and about 190 mL, between about 50 mL and about 180 mL, between about 50 mL and about 170 mL, between about 50 mL and about 180 mL, between about 50 mL and about 170 mL, between about 50 mL and about 160 mL, between about 50 mL and about 150 mL, between about 50 mL and about 140 mL, between about 50 mL and about 130 mL, between about 50 mL and about 120 mL, between about 50 mL and about 110 mL, between about 50 mL and about 100 mL, between about 50 mL and about 90 mL, between 50 mL and about 80 mL, between about 50 mL and about 70 mL, between about 50 mL and about 60 mL, between about 60 mL to about 1100 mL, between about 60 mL and about 1000 mL, between about 60 mL and about 800 mL, between about 60 mL and about 600 mL, between about 60 mL and about 400 mL, between about 60 mL and about 300 mL, between about 60 mL and about 200 mL, between about 60 mL and about 190 mL, between about 60 mL and about 180 mL, between about 60 mL and about 170 mL, between about 60 mL and about 160 mL, between about 60 mL and about 150 mL, between about 60 mL and about 140 mL, between about 60 mL and about 130 mL, between about 60 mL and about 120 mL, between about 60 mL and about 110 mL, between about 60 mL and about 100 mL, between about 60 mL and about 90 mL, between about 60 mL and about 80 mL, between about 60 mL and about 70 mL, between about 80 mL and about 1100 mL, between about 80 mL and about 1000 mL, between about 80 mL and about 800 mL, between about 80 mL and about 600 mL, between about 80 mL and about 400 mL, between about 80 mL and about 300 mL, between about 80 mL and about 200 mL, between about 80 mL and about 190 mL, between about 80 mL and about 180 mL, between about 80 mL and about 170 mL, between about 80 mL and about 160 mL, between about 80 mL and about 150 mL, between about 80 mL and about 140 mL, between about 80 mL and about 130 mL, between about 80 mL and about 120 mL, between about 80 mL and about 110 mL, between about 80 mL and about 100 mL, between about 80 mL and about 90 mL, between about 100 mL and about 1100 mL, between about 100 mL and about 1000 mL, between about 100 mL and about 800 mL, between about 100 mL and about 600 mL, between about 100 mL and about 400 mL, between about 100 mL and about 300 mL, between about 100 mL and about 200 mL, between about 100 mL and about 190 mL, between about 100 mL and about 180 mL, between about 100 mL and about 170 mL, between about 100 mL and about 160 mL, between about 100 mL and about 150 mL, between about 100 mL and about 140 mL, between about 100 mL and about 130 mL, between about 100 mL and about 120 mL, between about 100 mL and about 110 mL, between about 120 mL and about 1100 mL, between about 120 mL and about 1000 mL, between about 120 mL and about 800 mL, between about 120 mL and about 600 mL, between about 120 mL and about 400 mL, between about 120 mL and about 300 mL, between about 120 mL and about 200 mL, between about 120 mL and about 190 mL, between about 120 mL and about 180 mL, between about 120 mL and about 170 mL, between about 120 mL and about 160 mL, between about 120 mL and 150 mL, between about 120 mL and about 140 mL, between about 120 mL and about 130 mL, between about 140 mL and about 1100 mL, between about 140 mL and about 1000 mL, between about 140 mL and about 800 mL, between about 140 mL and about 600 mL, between about 140 mL and about 400 mL, between about 140 mL and about 300 mL, between about 140 mL and about 200 mL, between about 140 mL and about 190 mL, between about 140 mL and about 180 mL, between about 140 mL and about 170 mL, between about 140 mL and about 160 mL, between about 140 mL and about 150 mL, between about 160 mL and about 1100 mL, between about 160 mL and about 1000 mL, between about 160 mL and about 800 mL, between about 160 mL and about 600 mL, between about 160 mL and about 500 mL, between about 160 mL and about 400 mL, between about 160 mL and about 300 mL, between about 160 mL and about 200 mL, between about 160 mL and about 190 mL, between about 160 mL and about 180 mL, between about 160 mL and about 170 mL, between about 180 mL and about 1100 mL, between about 180 mL and about 1000 mL, between about 180 mL and about 800 mL, between about 180 mL and about 600 mL, between about 180 mL and about 400 mL, between about 180 mL and about 300 mL, between about 180 mL and about 200 mL, between about 180 mL and about 190 mL, between about 200 mL and about 1100 mL, between about 200 mL and about 1000 mL, between about 200 mL and about 800 mL, between about 200 mL and about 600 mL, between about 200 mL and about 400 mL, between about 400 mL and about 1100 mL, 400 mL and about 1000 mL, between about 400 mL and about 800 mL, between about 400 mL and about 600 mL, between about 600 mL and about 1100 mL, between about 600 mL and about 1000 mL, between about 600 mL and about 800 mL, between about 800 mL and about 1100 mL, between about 800 mL and about 1000 mL, or between about 900 mL and about 2100 mL.

The total volume of the base solution (e.g., alkali base solution) added to the culture over the entire culturing period can be between about 1% and about 7% (e.g., between about 1% and about 6%, between about 1% and about 5%, between about 1% and about 4%, between about 1% and about 3%, between about 1% and about 2%, between about 2% and about 7%, between about 2% and about 6%, between about 2% and about 5%, between about 2% and about 4%, between about 2% and about 3%, between about 3% and about 7%, between about 3% and about 6%, between about 3% and about 5%, between about 3% and about 4%, between about 4% and about 7%, between about 4% and about 6%, between about 4% and about 5%, between about 5% and about 7%, between about 5% and about 6%, or between about 6% and about 7%) of the volume of the first culture medium or the volume of the culture following inoculation but before the addition of fed culture medium.

The continuous addition of the base solution (e.g., alkali base solution) can take place over a period of between about 70 hours to about 125 hours (e.g., between about 70 hours to about 120 hours, between about 70 hours to about 110 hours, between about 70 hours to about 100 hours, between about 70 hours to about 90 hours, between about 70 hours to about 80 hours, between about 80 hours to about 125 hours, between about 80 hours to about 120 hours, between about 80 hours to about 110 hours, between about 80 hours to about 100 hours, between about 80 hour to about 90 hours, between about 90 hours to about 125 hours, between about 90 hours to about 120 hours, between about 90 hours to about 110 hours, between about 90 hours to about 100 hours, between about 92 hours to about 100 hours, between about 100 hours to about 125 hours, between about 100 hours to about 120 hours, between about 100 hours to about 110 hours, between about 110 hours to about 125 hours, between about 110 hours to about 120 hours, or between about 120 hours to about 125 hours.

Addition of Anti-Foam

Some embodiments of any of the methods described herein further including adding anti-foam to the first culture medium during fed batch culturing. The amount of anti-foam to be added to a fed batch culture is well-known in the art. For example, anti-foam can be added to the first culture medium in approximately 1 mL aliquots, as necessary to control foaming.

Agitation

The fed batch culturing of the cells usually includes some form of agitation for mixing of the culture. For example, the agitation used in fed batch culturing can be rotary agitation using an impeller. The agitation can occur at a frequency of at about 40 RPM to about 80 RPM (e.g., about 40 RPM to about 75 RPM, about 40 RPM to about 70 RPM, 40 RPM to about 65 RPM, about 40 RPM to about 60 RPM, about 40 RPM to about 55 RPM, about 40 RPM to about 50 RPM, about 40 RPM to about 45 RPM, about 45 RPM to about 80 RPM, about 45 RPM to about 75 RPM, about 45 RPM to about 70 RPM, about 45 RPM to about 65 RPM, about 45 RPM to about 60 RPM, about 45 RPM to about 55 RPM, about 45 RPM to about 50 RPM, about 50 RPM to about 80 RPM, about 50 RPM to about 75 RPM, about 50 RPM to about 70 RPM, about 50 RPM to about 65 RPM, about 50 RPM to about 60 RPM, about 50 RPM to about 55 RPM, about 55 RPM to about 80 RPM, about 55 RPM to about 75 RPM, about 55 RPM to about 70 RPM, about 55 RPM to about 65 RPM, about 55 RPM to about 60 RPM, about 60 RPM to about 80 RPM, about 60 RPM to about 75 RPM, about 60 RPM to about 70 RPM, about 60 RPM to about 65 RPM, about 65 RPM to about 80 RPM, about 65 RPM to about 75 RPM, about 65 RPM to about 70 RPM, about 70 RPM to about 80 RPM, about 70 RPM to about 75 RPM, or about 75 RPM to about 80 RPM. The agitation can be performed continuously or periodically.

Temperature

The fed batch culturing step described herein can be performed at a temperature of about 32° C. to about 39° C. (e.g., about 32° C. to about 38.5° C., about 32° C. to about 38° C., about 32° C. to about 37.5° C., about 32° C. to about 37° C., about 32° C. to about 36.5° C., about 32° C. to about 36° C., about 32° C. to about 35.5° C., about 32° C. to about 35° C., about 32° C. to about 34.5° C., about 32° C. to about 34° C., about 32° C. to about 33.5° C., about 32° C. to about 33° C., about 32° C. to about 32.5° C., about 32.5° C. to about 39° C., about 32.5° C. to about 38.5° C., about 32.5° C. to about 38° C., about 32.5° C. to about 37.5° C., about 32.5° C. to about 37° C., about 32.5° C. to about 36.5° C., about 32.5° C. to about 36° C., about 32.5° C. to about 35.5° C., about 32.5° C. to about 35° C., about 32.5° C. to about 34.5° C., about 32.5° C. to about 34° C., about 32.5° C. to about 33.5° C., about 32.5° C. to about 33° C., about 33° C. to about 39° C., about 33° C. to about 38.5° C., about 33° C. to about 38° C., about 33° C. to about 37.5° C., about 33° C. to about 37° C., about 33° C. to about 36.5° C., about 33° C. to about 36° C., about 33° C. to about 35.5° C., about 33° C. to about 35° C., about 33° C. to about 34.5° C., about 33° C. to about 34° C., about 33° C. to about 33.5° C., about 33.5° C. to about 39° C., about 33.5° C. to about 38.5° C., about 33.5° C. to about 38° C., about 33.5° C. to about 37.5° C., between about 33.5° C. to about 37° C., about 33.5° C. to about 36.5° C., about 33.5° C. to about 36° C., about 33.5° C. to about 35.5° C., about 33.5° C. to about 35° C., about 33.5° C. to about 34.5° C., about 33.5° C. to about 34° C., about 34° C. to about 39° C., about 34° C. to about 38.5° C., about 34° C. to about 38° C., about 34° C. to about 37.5° C., about 34° C. to about 37° C., about 34° C. to about 36.5° C., about 34° C. to about 36° C., about 34° C. to about 35.5° C., about 34° C. to about 35° C., about 34° C. to about 34.5°, about 34.5° C. to about 39° C., about 34.5° C. to about 38.5° C., about 34.5° C. to about 38° C., about 34.5° C. to about 37.5° C., about 34.5° C. to about 37° C., about 34.5° C. to about 36.5° C., about 34.5° C. to about 36° C., about 34.5° C. to about 35.5° C., about 34.5° C. to about 35° C., about 35° C. to about 39° C., about 35° C. to about 38.5° C., about 35° C. to about 38° C., about 35° C. to about 37.5° C., about 35° C. to about 37° C., about 35° C. to about 36.5° C., about 35° C. to about 36° C., about 35° C. to about 35.5° C., about 35.5° C. to about 39° C., about 35.5° C. to about 38.5° C., about 35.5° C. to about 38° C., about 35.5° C. to about 37.5° C., about 35.5° C. to about 37° C., about 35.5° C. to about 36.5° C., about 35.5° C. to about 36° C., about 36° C. to about 39° C., about 36° C. to about 38.5° C., about 36° C. to about 38° C., about 36° C. to about 37.5° C., about 36° C. to about 37° C., about 36° C. to about 36.5° C., about 36.5° C. to about 39° C., about 36.5° C. to about 38.5° C., about 36.5° C. to about 38° C., about 36.5° C. to about 37.5° C., about 36.5° C. to about 37° C., about 37° C. to about 39° C., about 37° C. to about 38.5° C., about 37° C. to about 38° C., about 37° C. to about 37.5° C., about 37.5° C. to about 39° C., about 37.5° C. to about 38.5° C., about 37.5° C. to about 38° C., about 38° C. to about 39° C., about 38° C. to about 38.5° C., or about 38.5° C. to about 39° C.). For example, the NS0 can be incubated at a temperature of about 36.5° C. from the beginning to the end of the culturing period. Skilled practitioners will appreciate that the temperature can be changed or may vary slightly during the culturing period, e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, or fifteen days after the start of the culturing period, or at any time point within the culturing period. For example, the temperature can be shifted upwards by about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0° C. In another example, the temperature can be shifted downwards by about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10° C.

$CO_2$

The fed batch culturing step can be performed using an atmosphere containing about 1% to 15% $CO_2$, at most or about 14% $CO_2$, 13% $CO_2$, 12% $CO_2$, 11% $CO_2$, 10% $CO_2$, 9% $CO_2$, 8% $CO_2$, 5% $CO_2$, 6% $CO_2$, 5% $CO_2$, 4% $CO_2$, 3% $CO_2$, 2% $CO_2$, or at most or about 1% $CO_2$. Methods for sparging $CO_2$ into a production bioreactor are well known in the art.

Any of the methods described herein can also include fed batch culturing the cells during the first time period in a humidified atmosphere comprising at least or about 20%, 30%, 40%, 50%, 60%, 70%, 85%, 80%, 85%, 90%, or at least or about 95% humidity, or about 100% humidity.

$dO_2$

The fed batch culturing step can be performed by maintaining a dissolved oxygen ($dO_2$) in the cell culture of between about 10% and about 20% (e.g., between about 10% and about 19%, between about 10% and about 18%, between about 10% and about 17%, between about 10% and about 16%, between about 10% and about 15%, between about 10% and about 14%, between about 10% and about 13%, between about 10% and about 12%, between about 10% and about 11%, between about 11% and about 20%, between about 11% and about 19%, between about 11% and about 18%, between about 11% and about 17%, between about 11% and about 16%, between about 11% and about 15%, between about 11% and about 14%, between about 11% and about 13%, between about 11% and about 12%, between about 12% and about 20%, between about 12% and about 19%, between about 12% and about 18%, between about 12% and about 17%, between about 12% and about 16%, between about 12% and about 15%, between about 12% and about 14%, between about 12% and about 13%, between about 13% and about 20%, between about 13% and about 19%, between about 13% and about 18%, between about 13% and about 17%, between about 13% and about 16%, between about 13% and about 15%, between about 13% and about 14%, between about 14% and about 20%, between about 14% and about 19%, between about 14% and about 18%, between about 14% and about 17%, between about 14% and about 16%, between about 14% and about 15%, between about 15% and about 20%, between about 15% and about 19%, between about 15% and about 18%, between about 15% and about 17%, between about 15% and about 16%, between about 16% and about 20%, between about 16% and about 19%, between about 16% and about 18%, between about 16% and about 17%, between about 17% and about 20%, between about 17% and about 19%, between about 17% and about 18%, between about 18% and about 20%, between about 18% and about 19%, or between about 19% and about 20%).

pH

During the fed batch culturing step, the pH of the cell culture can be maintained at a specific pH value by the addition of a base solution, such as an alkali base solution (as described above). The pH of a cell culture can be maintained at a pH of between about 6.5 and about 7.5 (e.g., between about 6.5 and about 7.4, between about 6.5 and about 7.3, between about 6.5 and about 7.2, between about 6.5 and about 7.1, between about 6.5 and about 7.0, between about 6.5 and about 6.9, between about 6.5 and about 6.8, between about 6.5 and about 6.7, between about 6.5 and about 6.6, between about 6.6 and about 7.5, between about 6.6 and about 7.4, between about 6.6 and about 7.3, between about 6.6 and about 7.2, between about 6.6 and about 7.1, between about 6.6 and about 7.0, between about 6.6 and about 6.9, between about 6.6 and about 6.8, between about 6.6 and about 6.7, between about 6.7 and about 7.5, between about 6.7 and about 7.4, between about 6.7 and about 7.3, between about 6.7 and about 7.2, between about 6.7 and about 7.1, between about 6.7 and about 7.0, between about 6.7 and about 6.9, between about 6.7 and about 6.8, between about 6.8 and about 7.5, between about 6.8 and about 7.4, between about 6.8 and about 7.3, between about 6.8 and about 7.2, between about 6.8 and about 7.1, between about 6.8 and about 7.0, between about 6.8 and about 6.9, between about 6.9 and about 7.5, between about 6.9 and about 7.4, between about 6.9 and about 7.3, between about 6.9 and about 7.2, between about 6.9 and about 7.1, between about 6.9 and about 7.0, between about 7.0 and about 7.5, between about 7.0 and about 7.4, between about 7.0 and about 7.3, between about 7.0 and about 7.2, between about 7.0 and about 7.1, between about 7.1 and about 7.5, between about 7.1 and about 7.4, between about 7.1 and about 7.3, between about 7.1 and about 7.2, between about 7.2 and about 7.5, between about 7.2 and about 7.4, between about 7.2 and about 7.3, between about 7.3 and about 7.5, between about 7.3 and about 7.4, or between about 7.4 and about 7.5).

Eculizumab

The recombinant protein produced by the mammalian cells cultured in any of the methods described herein can be a recombinant eculizumab including a heavy chain including SEQ ID NO: 1 and a light chain including SEQ ID NO: 2. The recombinant protein produced by the mammalian cells cultured in any of the methods described herein can be a recombinant eculizumab including a heavy chain of SEQ ID NO: 1 and a light chain of SEQ ID NO: 2.

Nucleic acid that encodes the heavy and light chains of eculizumab are known in the art (see, for example, the nucleic acid sequences in U.S. Pat. No. 6,355,245 and Fc region sequences in An et al., *mAbs* 1:6, 572-579, 2009).

Assessing One or More Cell Culture Parameters

Some embodiments of any of the methods described herein further include assessing one or more cell culture parameters in the fed batch culture. Non-limiting examples of cell culture parameters include: cell growth, percentage cell viability, viable cell density, aerobic glucose consumption, eculizumab titer, specific productivity rate, volumetric productivity rate, lactate levels, eculizumab quality (e.g., fragmentation and binding affinity), lactate production, glucose levels, and pH.

Methods that can be used to assess the one or more cell culture parameters are well-known in the art. For example, cell growth and percentage cell viability can be determined using, e.g., a ViCell XR automated cell counter. The amount of eculizumab present in the culture can be determined using spectrophotometric absorbance or a Bradford protein assay. The amount of eculizumab present in the culture can be determined as a titer by serial dilution. Glucose levels and lactate levels can be determined using methods well known in the art, e.g., glucose assay kit and the L-lactate assay kits sold by Abcam. The pH in the fed batch culture can be determined, e.g., by placing a pH probe in the culture.

The one or more assessed cell culture parameters can be compared to the same one or more cell culture parameters determined in a large-scale eculizumab production cell culture.

Collecting the Eculizumab

Some embodiments of any of the methods described herein further include a step of collecting the recombinant eculizumab produced in the fed batch culturing step. In some examples, the collecting includes lysing the mammalian cells. In some examples, the recombinant eculizumab is collected from the culture medium (e.g., one or both of the first liquid culture medium and the feed culture medium, or one, two, or three of the first liquid culture medium, the first liquid feed culture medium, and the second liquid feed culture medium). Methods for lysing a mammalian cells are well known in the art. Methods for collecting a recombinant antibody (such as eculizumab) from media are well-known in the art, and include, e.g., affinity chromatography and/or filtration.

Purifying the Collected Eculizumab

Some embodiments of any of the methods described herein further include a step of purifying the collected recombinant eculizumab. As is known in the art, a collected recombinant antibody (such as eculizumab) can be purified using methods known in the art. For example, one or more steps of filtration and chromatography (e.g., affinity chromatography (e.g., using a protein A resin), anionic exchange chromatography, cation exchange chromatography, molecular sieve chromatography, and hydrophobic interaction chromatography) can be formed to purify the collected recombinant antibody (e.g., eculizumab). Additional methods for purifying a collected recombinant antibody (e.g., eculizumab) are well known in the art.

The purified recombinant eculizumab can be substantially free (such as at least or about 90% free, or about 95%, 96%, 97%, 98%, or at least or about 99% free) of contaminating proteins from a liquid culture medium and/or contaminating DNA, proteins, lipids, and carbohydrates from the lysate of a mammalian cell.

Shifting the Isoelectric Profile of the Collected or Purified Eculizumab

In some examples, the isoelectric profile of the collected or purified recombinant eculizumab may be shifted (shifted to a more acidic isoelectric profile) using the methods described in U.S. Provisional Patent Application No. 62/064,397, filed Oct. 15, 2014, which is incorporated by reference herein.

Formulating the Eculizumab

Some embodiments of any of the methods described herein further include formulating the collected recombinant eculizumab, the purified recombinant eculizumab, or the shifted recombinant eculizumab into a pharmaceutical composition. Formulating the collected recombinant eculizumab, the purified recombinant eculizumab, or the shifted recombinant eculizumab into a pharmaceutical composition can include the step of mixing or adding the purified recombinant eculizumab, the collected recombinant eculizumab, or the shifted recombinant eculizumab to a pharmaceutically acceptable excipient to generate the pharmaceutical composition. Examples of pharmaceutically acceptable excipients (e.g., non-naturally occurring pharmaceutically acceptable excipients) are well known in the art.

EXAMPLES

The invention is further described in the following examples, which do not limit the scope of the invention described in the claims.

Figure 2:
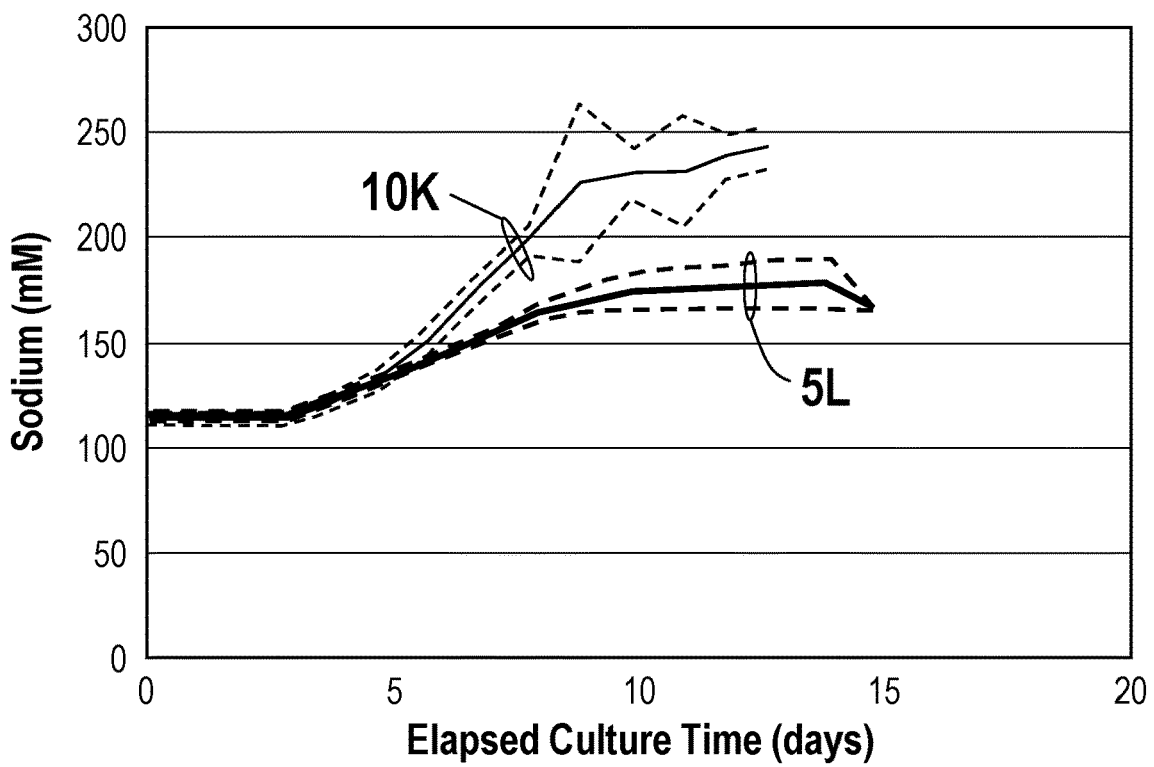
FIG. 2 is a graph showing the mean concentration (solid lines) of sodium over time in 10,000-L eculizumab production cell cultures (thin solid black lines) and previous 5-L eculizumab small scale cultures (thick solid black lines). The dashed lines represent ±1 standard deviation of the data.
Figure 3:
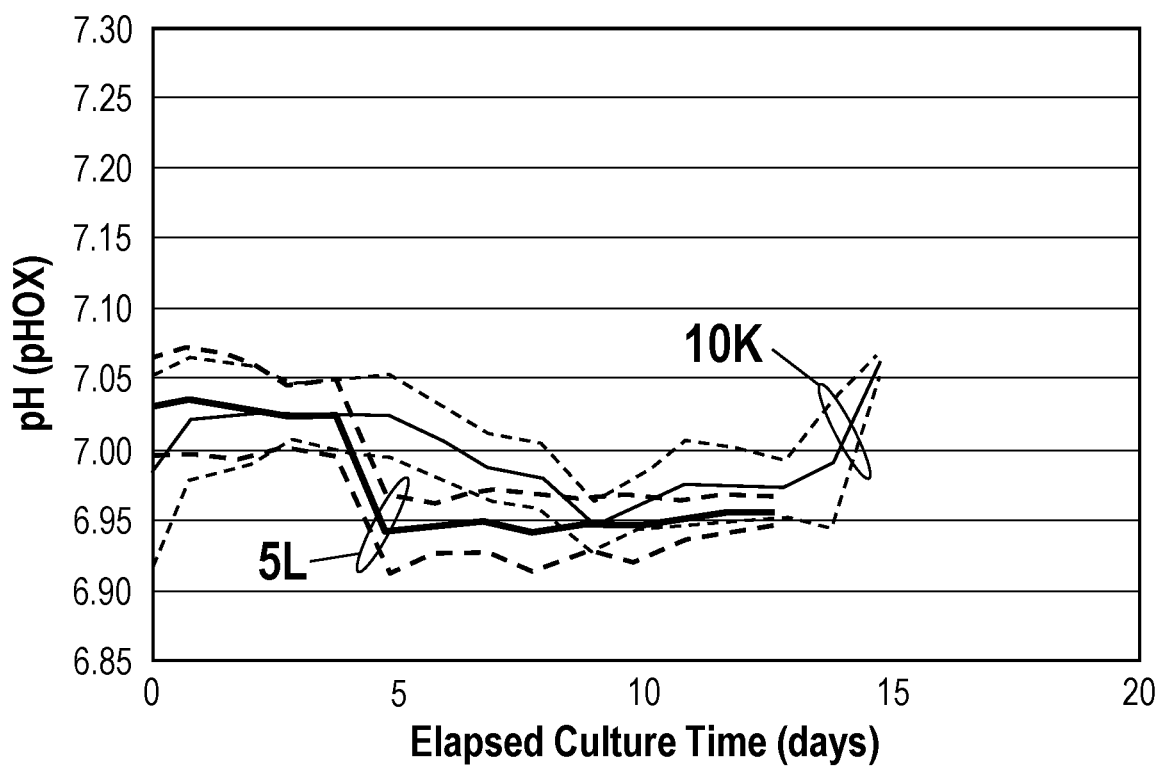
FIG. 3 is a graph showing the mean offline pH over time in 10,000-L eculizumab production cell cultures (thin solid black lines) and previous 5-L eculizumab small scale cultures (thick solid black lines). The dashed lines represent ±1 standard deviation of the data.
Figure 4:
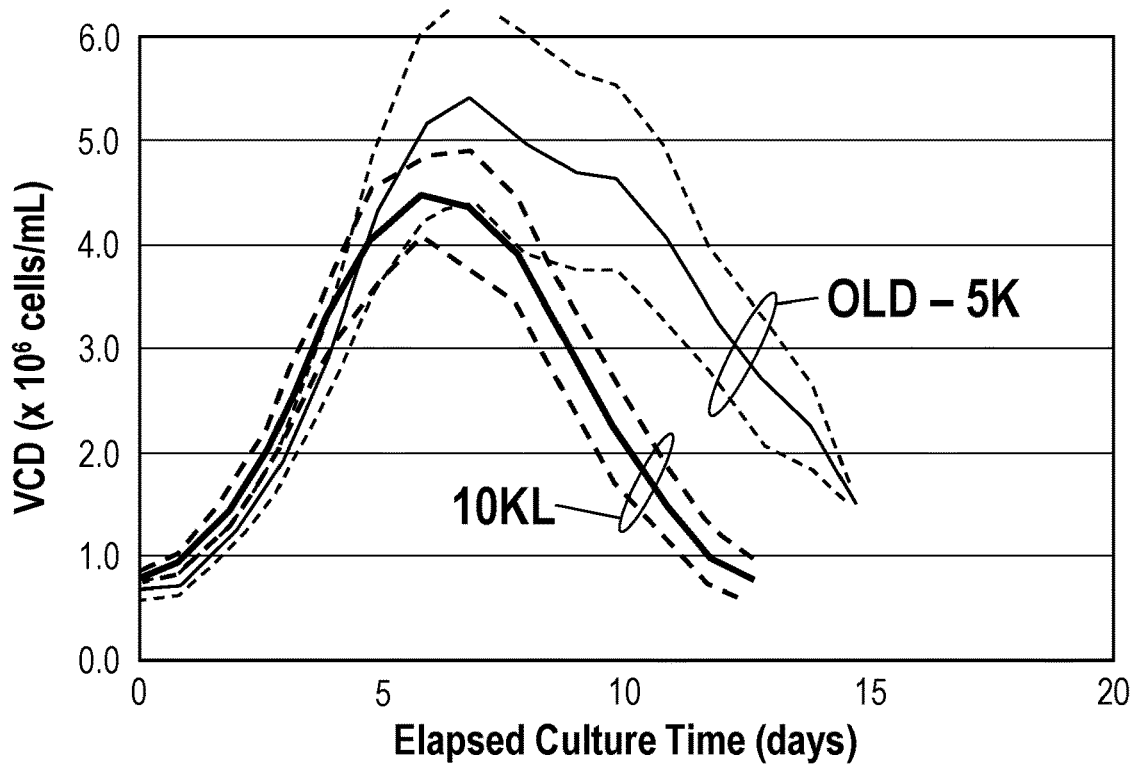
FIG. 4 is a graph showing the mean viable cell density over time in 10,000-L eculizumab production cell cultures (thick solid black lines) and previous 5-L eculizumab small scale cultures (thin solid black lines). The dashed lines represent ±1 standard deviation of the data.

Example 1. Previous Attempts at Replicating an Eculizumab Production Cell Culture Eculizumab is typically produced using a 10,000-L fed batch mammalian cell culture. The mammalian cells in the production cell culture secrete recombinant eculizumab into the culture medium during the culturing period. Previous attempts were made to try to replicate the culture parameters observed in a 10,000-L eculizumab production cell culture. The previous attempts at replicating a 10,000-L eculizumab production cell culture were unsuccessful, as the previous small scale cultures showed, e.g., a decreased level of lactate in the culture over time, decreased sodium in the culture over time, and a different trend in pH over time as compared to a 10,000-L eculizumab production cell culture (see FIGS. 1, 2, and 3, respectively). In addition, the previous small scale cultures showed an increase in viable cell density over time, an increased percentage cell viability at later time points during the culturing period, increased titers of eculizumab at later time points during the culturing period, and increased glucose concentration in the culture at later time points during the culturing period (see, FIGS. 4, 6, 8, and 10, respectively).

Example 2. New Small Scale Cultures for Accurately Replicating an Eculizumab Production Cell Culture A new small scale model was developed and tested to determine if the new cell small-scale culture model would accurately replicate culture parameters of a 10,000-L eculizumab production cell culture.

The newly developed small scale culture was cultured using the following methods. An Applikon 7-L vessel was used to incubate the culture. The Applikon 7-L vessel contains a L-type drilled hole sparger and overlay port for the introduction of gasses to the vessel, four 12-mm ports (for the pH sensor, dissolved oxygen sensor, a septum, and the exhaust condenser), a triple addition top-port, sample/harvest dip tube, and an overhead motor driven impeller shaft. Tubing was attached to these ports in order to connect the vessel to the gas supply systems, external controls, and the two different liquid feed culture media, the base solution, and the lipid solution given to the bioreactor during the culturing period.

The bioreactor was autoclaved using 5-10 mL of deionized water for internal steam generation. Prior to inoculation, 3.7 L of a first liquid culture medium was added to the bioreactor. The media was then held at 36.5° C., with air and carbon dioxide sparging and an initial agitation of 60 RPM. Within 6 hours prior to inoculation, 3.7 mL of a first lipid solution containing linoleic acid, oleic acid, and cholesterol was added to the bioreactor through the head plate septum. The pH and $dO_2$ sensors were standardized before inoculation, and the $dO_2$ sensor was calibrated to 100% air saturation after the first lipid solution was added, but prior to inoculation.

A seed-train NS0 cell culture was used to calculate the exact volume of the seed-train NS0 cell culture to be added to the bioreactor to generate (after inoculation) an initial viable cell density of $5\times10^5$ cells/mL and an initial culture volume of 4.2 L. The cell culture was then cultured using a rotary agitation rate of 60 RPM, a temperature of 36.5° C., a pH of 7.00, and a $dO_2$ of 15%. The gassing strategy used was to use 0 to 30.0 SLPH air, with up to 30.0 SLPH additional $O_2$ cumulative as needed on demand to maintain the $dO_2$ set point of 15%. The air overlay used was 225 mL/minute air. At day 0 to day 5 of the culturing period, the pH set point was set to pH 7.00±0.05. At day 5 to day 9 of the culturing period (or 48 hours after the start of the feed if the target cell density is met on day 2 of the culture), the pH set point was set to pH 7.00±0.25. At day 10 to culture harvest, the pH set point was set to pH 7.00±0.05.

Once the cell culture achieved a target cell density of equal to or greater than $18\times10^5$ cells/mL a 1 mL/L bolus addition of a second lipid solution (containing oleic acid, linoleic acid, and cholesterol) was added to the bioreactor (typically 4.2 mL). Following the addition of the second lipid solution, the addition of two different liquid feed culture media (first and second liquid feed culture media) to the culture was initiated. One hundred sixty eight mLs of each of the first and the second liquid feed culture media were continuously added to the bioreactor over 5.5 days (133.3 hours). The net volume of the first liquid feed culture medium added over the 5.5 days was 4% of the initial culture volume. The net volume of the second liquid feed culture medium added over the 5.5 days was 4% of the initial culture volume. The feed of both the first and second liquid feed culture media typically occurs at approximately 72 hours after the initiation of the culturing period to approximately 205.3 hours after the initiation period. Both the first liquid feed culture medium and the second liquid feed culture medium were added to the culture in a multiple syringe pump set-up at approximately 21 µL per minute.

Gibco animal-origin free (AOF) FoamAway was added as needed in 1.0 mL shots through the head plate septum.

One hundred and sixty eight mL of a base solution containing 0.75 M sodium carbonate and 0.5 M sodium bicarbonate was continuously added over 96 hours to the culture with the continuous addition initiated at a time point that is approximately 48 hours after the start of the continuous addition of the first liquid feed culture medium and second liquid feed culture medium to the culture. Commonly, the base solution was continuously added to the culture between 120 hours after the start of the culturing period and 216 hours after the start of the culturing period. The base solution was added just above the culture liquid surface through the head plate triport line using a multi-syringe pump at a continuous flow on a per minute bases.

The viable cell density, the percentage cell viability, the eculizumab titer, and the glucose concentration in the culture over the culturing period in each small scale culture were determined using methods well-known in the art.

Figure 5:
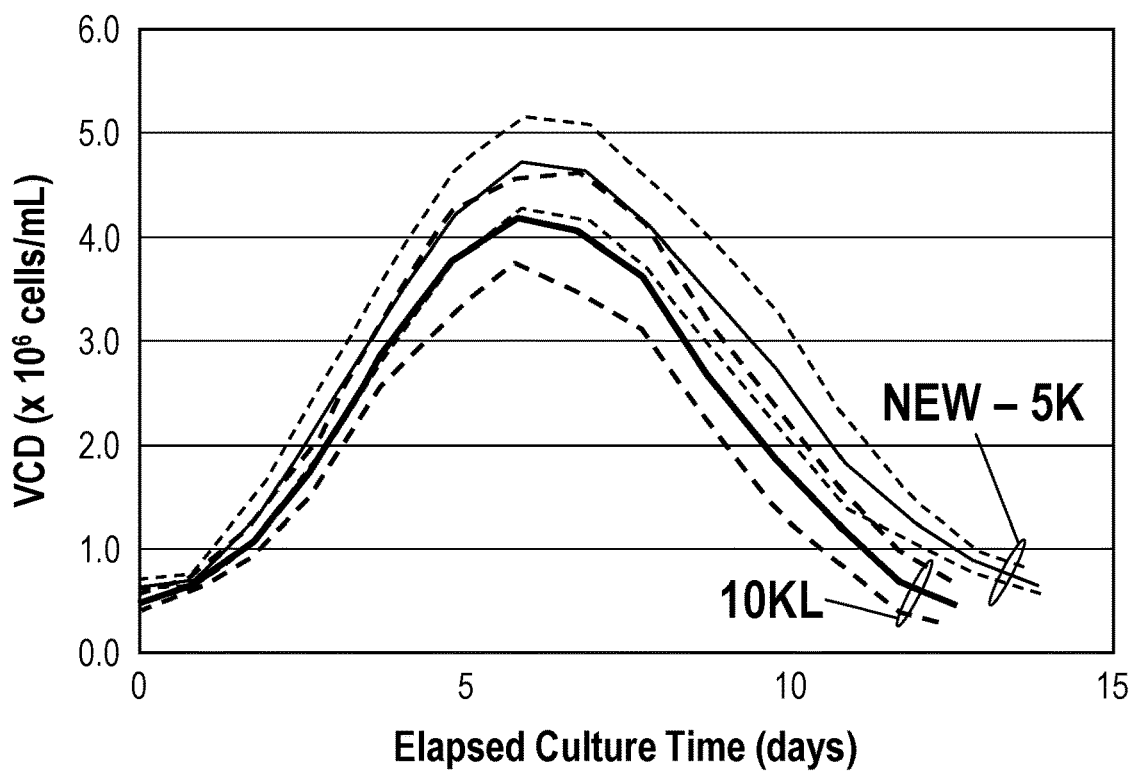
FIG. 5 is a graph showing the mean viable cell density over time in 10,000-L eculizumab production cell cultures (thick solid black lines) and 5-L eculizumab small scale cultures cultured using the methods described herein (thin solid black lines) (n=40). The dashed lines represent ±1 standard deviation of the data.
Figure 6:
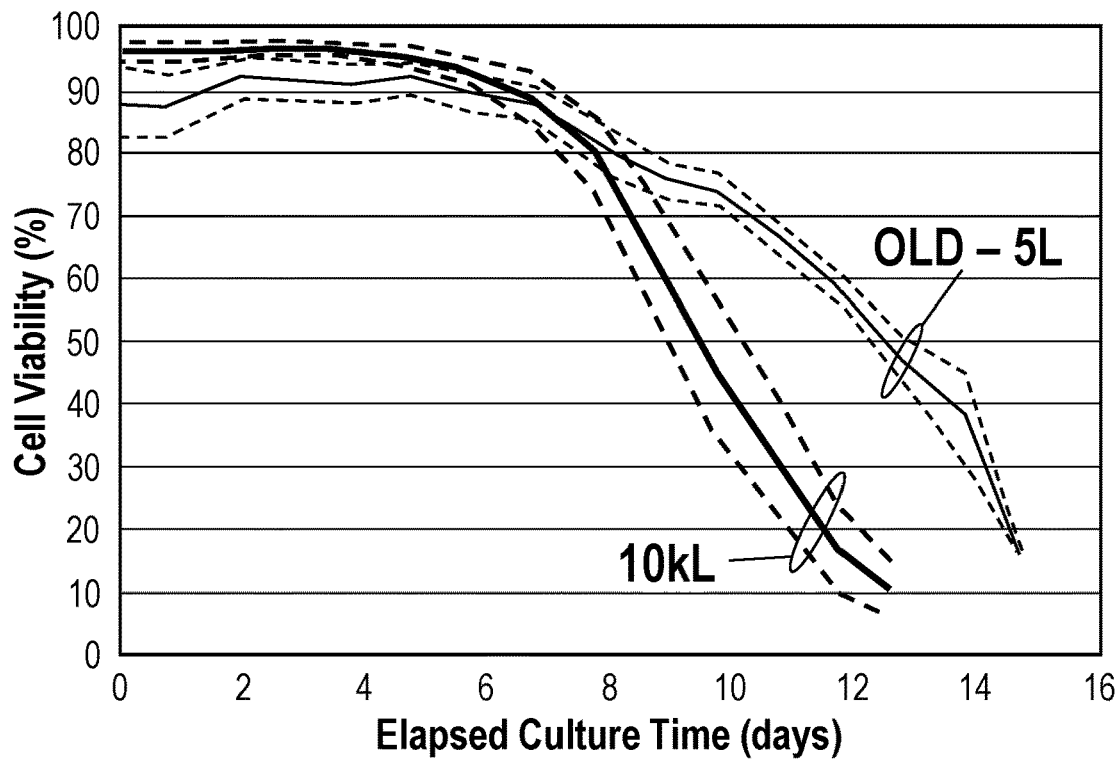
FIG. 6 is a graph showing the mean percentage cell viability over time in 10,000-L eculizumab production cell cultures (thick solid black lines) and previous 5-L eculizumab small scale cultures (thin solid black lines). The dashed lines represent ±1 standard deviation of the data.
Figure 7:
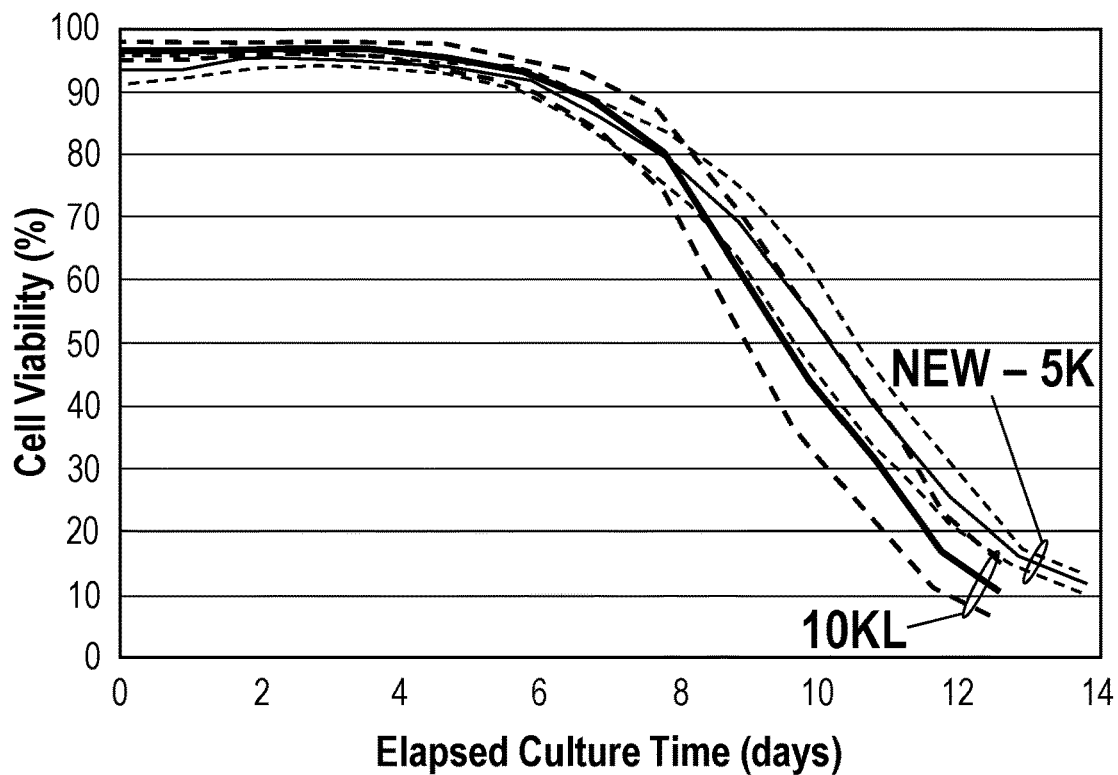
FIG. 7 is a graph showing the mean percentage cell viability over time in 10,000-L eculizumab production cell cultures (thick solid black lines) and 5-L eculizumab small scale cultures cultured using the methods described herein (thin solid black lines) (n=40). The dashed lines represent ±1 standard deviation of the data.
Figure 8:
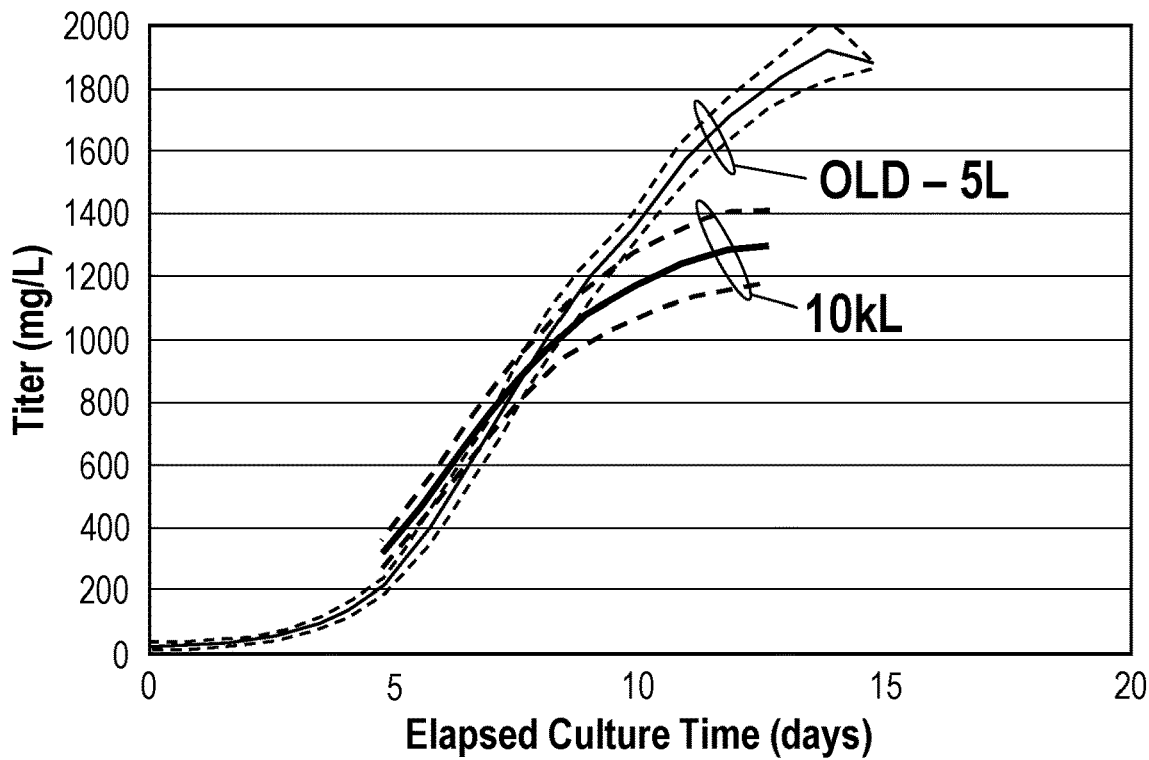
FIG. 8 is a graph showing the titer of eculizumab over time in 10,000-L eculizumab production cell cultures (thick solid black lines) and previous 5-L eculizumab small scale cultures (thin solid black lines). The dashed lines represent ±1 standard deviation of the data.
Figure 9:
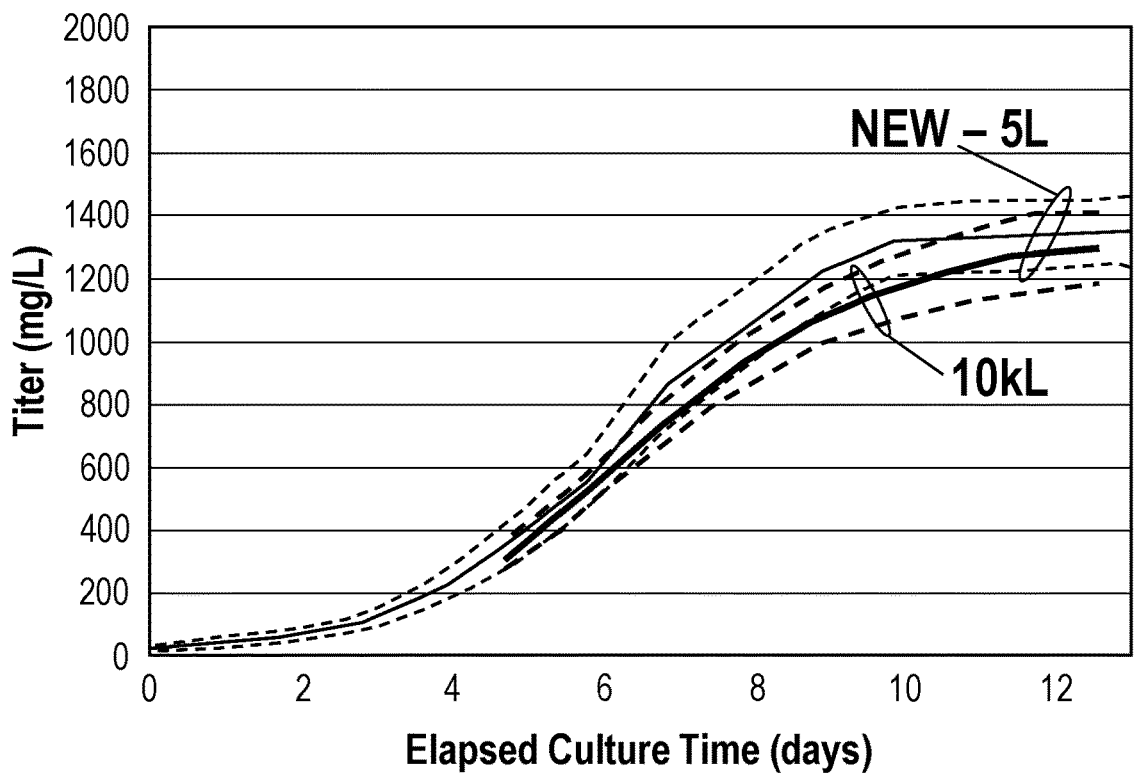
FIG. 9 is a graph showing the titer of eculizumab over time in 10,000-L eculizumab production cell cultures (thick solid black lines) and 5-L eculizumab small scale cultures cultured using the methods described herein (thin solid black lines) (n=40). The dashed lines represent ±1 standard deviation of the data.
Figure 10:
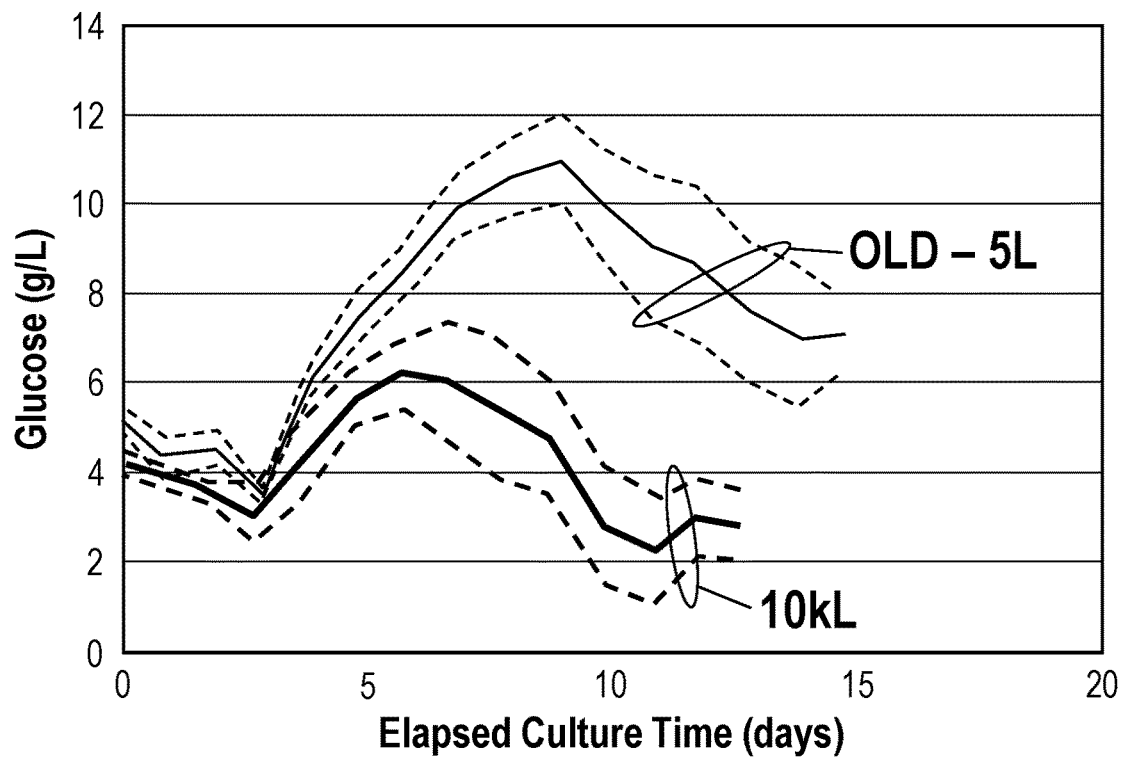
FIG. 10 is a graph showing the glucose concentration over time in 10,000-L eculizumab production cell cultures (thick solid black lines) and previous 5-L eculizumab small scale cultures (thin solid black lines). The dashed lines represent ±1 standard deviation of the data.
Figure 11:
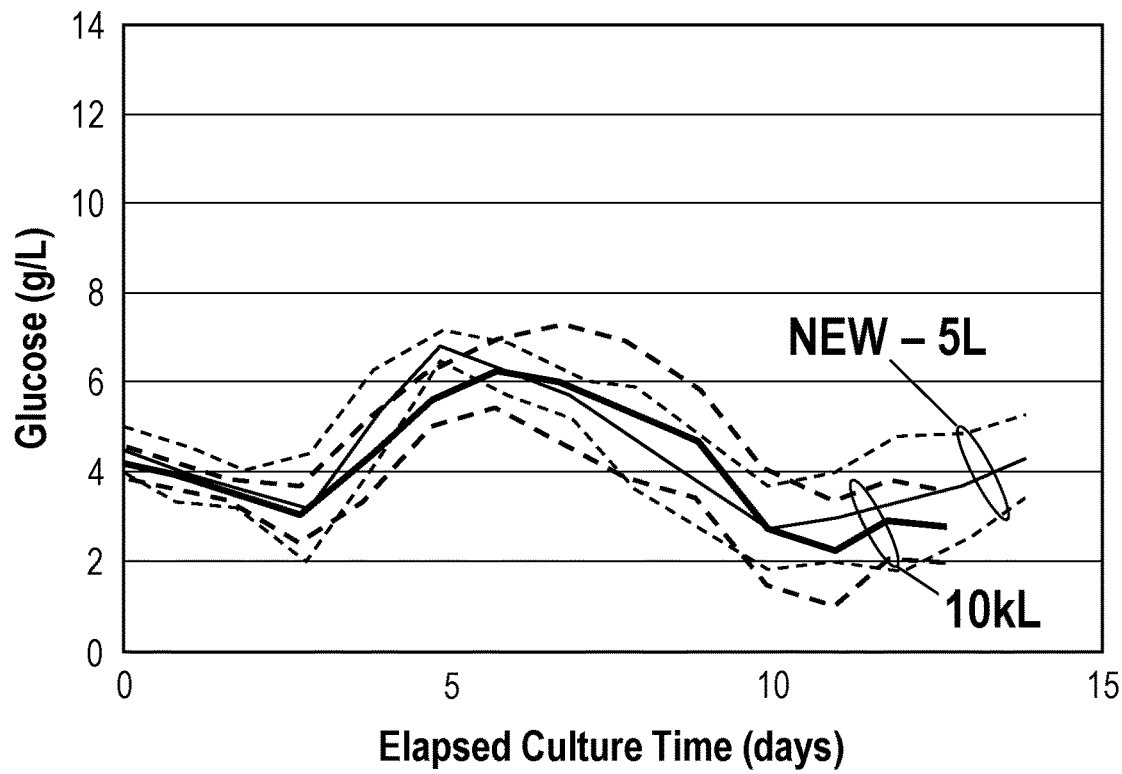
FIG. 11 is a graph showing the glucose concentration over time in 10,000-L eculizumab production cell cultures (thick solid black lines) and 5-L eculizumab small scale cultures cultured during the methods described herein (thin solid black lines) (n=40). The dashed lines represent ±1 standard deviation of the data.

The resulting data show that, in contrast with the previous small scale eculizumab cell culture, the newly developed small scale eculizumab fed batch cell culture is able to accurately replicate: the viable cell density over time in an eculizumab production cell culture (compare FIG. 5 with FIG. 4), the percentage cell viability over time in an eculizumab production cell culture (compare FIG. 7 with FIG. 6), the titer of eculizumab over time in an eculizumab production cell culture (compare FIG. 9 with FIG. 8), and the concentration of glucose over time in an eculizumab production cell culture (compare FIG. 11 with FIG. 10).

In sum, the data show that the small scale culturing methods provided herein accurately replicate at least four of the cell culture parameters of an eculizumab production cell culture.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Sequence Appendix
PRT
Homo sapiens
Eculizumab Heavy Chain

SEQ ID NO: 1

QVQLVQSGAEVKKPGASVKVSCKASGYIFSNYWIQWVRQAPGQGLEWMGE

ILPGSGSTEYTENFKDRVTMTRDTSTSTVYMELSSLRSEDTAVYYCARYF

FGSSPNWYFDVWGQGTLVTVSSASTKGPSVFPLAPCSRSTSESTAALGCL

VKDYFPEPVTVSWNSGALTSGVHTFPAVLQSSGLYSLSSVVTVPSSNFGT

QTYTCNVDHKPSNTKVDKTVERKCCVECPPCPAPPVAGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

PRT
Homo sapiens
Eculizumab Light Chain

SEQ ID NO: 2

DIQMTQSPSSLSASVGDRVTITCGASENIYGALNWYQQKPGKAPKLLIYG

ATNLADGVPSRFSGSGSGTDFTLTISSLQPEDFATYYCQNVLNTPLTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

What is claimed is:

1. A method of replicating a large-scale eculizumab production cell culture in a small scale culture, the method comprising:
    providing a 4-L to 10-L fed batch bioreactor containing a first culture medium that occupies between about 70% and about 90% of the capacity of the bioreactor and has an initial cell density of between about $2.5 \times 10^5$ and about $7.5 \times 10^5$ NSO cells/mL, the cells comprising a nucleic acid encoding a recombinant eculizumab heavy chain comprising SEQ ID NO: 1 and a recombinant eculizumab light chain comprising SEQ ID NO: 2,
    culturing the cells in the bioreactor for at least 8 days at about 34° C. to about 39° C., at a $dO_2$ level of between about 14% to about 16%, and a rotary agitation of between about 50 RPM and about 70 RPM;
    maintaining fed batch culturing until a cell density of about $13 \times 10^5$ to about $20 \times 10^5$ cells/mL is reached, then;
    (a) continuously adding a feed culture medium to the first culture medium for a period of about 120 hours to about 150 hours, and about 40 to 60 hours after the start of continuous addition of the feed culture medium, and
    (b) continuously adding an alkali base solution to the first culture medium for a period of between about 90 hours to about 105 hours,
    wherein one or both of the first culture medium and the feed culture medium comprises bovine serum albumin (BSA) processed from bovine plasma without heating to remove euglobulin and immunoglobulins.

2. The method of claim 1, wherein the processed BSA is processed from a bovine bred and raised in New Zealand.

3. The method of claim 1, wherein the initial cell density is between about $4.0 \times 10^5$ cells/mL and about $6.0 \times 10^6$ cells/mL.

4. The method of claim 1, wherein the fed batch culturing is performed at a temperature of about 36° C. to about 37° C.

5. The method of claim 1, wherein the rotary agitation is between about 55 RPM and about 65 RPM.

6. The method of claim 1, wherein the target cell density is between about $17 \times 10^5$ cells/mL and about $19 \times 10^5$ cells/mL.

7. The method of claim 1, wherein:
    (a) the alkali base solution is continuously added to the first culture medium for a period of between about 92 hours to about 100 hours; and/or
    (b) the alkali base solution comprises between about 0.65 M and about 0.85 M sodium carbonate and between about 0.4 M and about 0.6 M sodium bicarbonate.

8. The method of claim 7, wherein the bioreactor comprises 4.2 L of the first culture medium, and the alkali base solution is continuously added to the first culture medium at a rate of between about 1.65 mL/hour to about 1.85 mL/hour.

9. The method of claim 1, wherein a single feed culture medium is continuously added to the first culture medium.

10. The method of claim 1, wherein two different feed culture media are continuously added to the first culture medium.

11. The method of claim 10, wherein each of the two different feed culture media are continuously added to the first culture medium at a rate of between about 15 µL/minute to about 35 µL/minute.

12. The method of claim 11, wherein each of the two different feed culture media are continuously added to the first culture medium at a rate of between about 20 µL/minute to about 25 µL/minute.

13. The method of claim 1, wherein the feed culture medium is continuously added to the first culture medium for a period of between about 130 hours to about 135 hours.

14. The method of claim 1, further comprising adding a bolus of a lipid solution comprising linoleic acid, oleic acid, and cholesterol to the first culture medium at a time point when the cells reach a density of about $13 \times 10^5$ cells/mL to about $20 \times 10^5$ cells/mL.

15. The method of claim 14, wherein the lipid solution is added at a dose of about 1 mL per 1 L of the first culture medium.

16. The method of claim 1, further comprising:
    (a) adding anti-foam to the first culture medium during culturing; and/or
    (b) collecting the recombinant eculizumab produced in the culturing step.

17. The method of claim 1, wherein recombinant eculizumab is collected from one or both of the first culture medium and the feed culture medium.

18. The method of claim 1, further comprising assessing one of more cell culture parameters selected from the group consisting of: cell growth, percentage cell viability, viable cell density, aerobic glucose consumption, eculizumab titer, specific productivity rate, volumetric productivity rate, lactate production, and eculizumab quality.

19. The method of claim 1, wherein the BSA is produced by a method comprising
    (a) providing plasma from a bovine;
    (b) desalting the plasma;
    (c) precipitating and removing euglobulin out of the plasma;
    (d) performing ion exchange chromatography on the plasma to produce an eluate comprising serum albumin and immunoglobulins;
    (e) precipitating and removing the immunoglobulins from the eluate; and
    (f) concentrating and freeze-drying the eluate to produce lyophilized BSA.

20. The method of claim 19, wherein the lyophilized BSA is reconstituted into a solution prior to use.

* * * * *

SEQUENCE LISTING

<160> NUMBER OF SEQ ID NOS: 2

<210> SEQ ID NO 1
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```